United States Patent
Rigatti et al.

(10) Patent No.: US 9,677,132 B2
(45) Date of Patent: *Jun. 13, 2017

(54) POLYNUCLEOTIDE MODIFICATION ON SOLID SUPPORT

(71) Applicants: Illumina Cambridge Limited, Nr Saffron Walden (GB); Illumina, Inc., San Diego, CA (US)

(72) Inventors: Roberto Rigatti, Nr Saffron Walden (GB); Niall Anthony Gormley, Little Chesterford (GB); Allen E. Eckhardt, San Diego, CA (US); Jonathan Mark Boutell, Nr Saffron Walden (GB)

(73) Assignee: Illumina, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/575,863

(22) Filed: Dec. 18, 2014

(65) Prior Publication Data
US 2015/0197799 A1 Jul. 16, 2015

Related U.S. Application Data

(60) Provisional application No. 61/928,382, filed on Jan. 16, 2014.

(51) Int. Cl.
C12Q 1/68 (2006.01)

(52) U.S. Cl.
CPC ........ C12Q 1/6874 (2013.01); C12Q 1/6806 (2013.01); C12Q 1/6837 (2013.01); C12Q 1/6853 (2013.01)

(58) Field of Classification Search
None
See application file for complete search history.

(56) References Cited

U.S. PATENT DOCUMENTS

| | | | |
|---|---|---|---|
| 8,034,568 B2 * | 10/2011 | Kurn et al. | C12Q 1/686 435/6.12 |
| 8,728,764 B2 | 5/2014 | Boutell | |
| 2003/0232348 A1 | 12/2003 | Jones et al. | |
| 2005/0100900 A1 | 5/2005 | Kawashima et al. | |
| 2006/0078925 A1 * | 4/2006 | Mourelatos et al. | C12Q 1/6809 435/6.11 |
| 2012/0010087 A1 | 1/2012 | Shapero et al. | |
| 2012/0053063 A1 | 3/2012 | Rigatti et al. | |
| 2012/0122737 A1 | 5/2012 | Sabot et al. | |
| 2012/0157322 A1 | 6/2012 | Myllykangas et al. | |

FOREIGN PATENT DOCUMENTS

| WO | 2012/040387 | 3/2012 |
|---|---|---|
| WO | 2012/151111 | 6/2012 |

OTHER PUBLICATIONS

International Search Report for PCT Application No. PCT/EP2014/079145 dated Mar. 5, 2015.
Myllykangas, et al., "Efficient targeted resequencing of human germline and cancer genomes by oligonucleotide-selective sequencing", Nature Biotechnology, vol. 29, No. 11, Nov. 2011, 1024-1029.

* cited by examiner

*Primary Examiner* — Kaijiang Zhang
(74) *Attorney, Agent, or Firm* — Illumina, Inc.

(57) ABSTRACT

The present disclosure relates to the field of molecular biology and more specifically to methods for capturing and amplifying target polynucleotides on a solid surface.

18 Claims, 19 Drawing Sheets

POLYNUCLEOTIDE MODIFICATION ON SOLID SUPPORT

The present disclosure relates to the field of molecular biology and more specifically to methods for capturing and amplifying target polynucleotides on a solid surface.

BACKGROUND

Next generation sequencing has enabled whole genome sequencing and whole genome analysis. Next generation sequencing methods typically rely on the universal amplification of genomic fragments that are first equipped with universal amplification regions and then captured indiscriminately by universal capture primers on a solid surface. The universal capture primers mediate both polynucleotide capture and bridge amplification, a key element in next generation sequencing methods (see, e.g., WO 2011/025477 A1, US 2011/0172119 A1).

While current methods can effectively support the sequencing of entire genomes, they do not allow for the targeted capture of specific polynucleotides and therefore do not support, for example, the targeted sequencing of partial genomes. However, a growing need exists for methods facilitating the targeted sequencing of, for example, specific fractions of an organism's exome or transcriptome. This need is driven partly by cost but also by data handling considerations.

Thus, there exists a need for new methods that enable the targeted next generation sequencing of partial genomes. The present disclosure addresses this need by providing methods for modifying immobilized capture primers on a surface. Related advantages are provided as well.

SUMMARY

The present disclosure provides methods of modifying an immobilized capture primer.

In one aspect, the disclosure provides a method of modifying an immobilized capture primer including: a) providing a solid support having an immobilized application-specific capture primer, the application-specific capture primer including: i) a 3' portion including an application-specific capture region, and ii) a 5' portion including a universal capture region; b) contacting an application-specific polynucleotide with the application-specific capture primer under conditions sufficient for hybridization to produce an immobilized application-specific polynucleotide, and c) removing the application-specific capture region of an application-specific capture primer not hybridized to an application-specific polynucleotide to convert the unhybridized application-specific capture primer to a universal capture primer. In some embodiments, a portion of the application-specific capture region is removed.

In some embodiments, the application-specific capture primer comprises a plurality of different immobilized application-specific capture primers.

In some embodiments, the application-specific polynucleotide comprises a plurality of different application-specific polynucleotides.

In some embodiments, the application-specific capture region includes a target-specific capture region and the application-specific polynucleotide includes a target polynucleotide.

In some embodiments, the application-specific capture region includes a transposon end (TE) region and the application-specific polynucleotide includes a TE oligonucleotide.

In some embodiments, the method further includes applying an oligonucleotide before execution of step c) under conditions sufficient for oligonucleotide hybridization with the universal capture region of an application-specific capture primer to produce a double-stranded DNA region. In certain embodiments, the oligonucleotide is a P5 or P7 oligonucleotide.

In some embodiments, the method further includes applying an oligonucleotide before execution of step c) under conditions sufficient for oligonucleotide hybridization with the application-specific capture region of an application-specific capture primer to produce a double-stranded DNA region.

In some embodiments, the method further includes contacting the application-specific capture primer with a nuclease, wherein the application-specific capture region of an application specific capture primer not hybridized with an application-specific polynucleotide to is removed by the nuclease. In some embodiments, the nuclease is an exonuclease. In some embodiments, the exonuclease is exonuclease I. In some embodiments, the exonuclease is exonuclease III. In some embodiments, the nuclease is an endonuclease.

In some embodiments, providing solid support includes immobilizing the application-specific capture primer onto the solid support. In some embodiments, the application-specific capture primer is immobilized directly onto the solid support. In some embodiments, the immobilization of the application-specific capture primer includes immobilizing a universal capture primer onto the solid support. In some embodiments, the method further includes converting the immobilized universal capture primer into the application-specific capture primer.

BRIEF DESCRIPTION OF THE DRAWINGS

FIG. 2 also exemplifies the hybridization and extension method of converting a universal capture primer into an application-specific capture primer.

FIG. 5 also illustrates that an immobilized target polynucleotide can occasionally mis-hybridize with a non-matching target-specific probe, e.g., with its universal capture region. Mis-hybridized target polynucleotides cannot effectively support capture primer extension.

FIG. 9 shows the imaging results after the flowcell was hybridized with labeled anti-P5 and anti-P7 oligonucleotides (A). FIG. 9 also shows the imaging results following the subsequent removal of labeled anti-P5 and anti-P7 oligonucleotides and hybridization of the flowcell with labeled anti-ME oligonucleotides (B). After removal of the labeled anti-ME oligonucleotides, lanes 3, 6, 7, and 8 of the flowcell were hybridized with unlabeled anti-P5 and anti-P7 oligonucleotides. Lanes 4, 5, 6 and 8 were then subjected to exonuclease I treatment. After removal of the unlabeled anti-P5 and anti-P7 oligonucleotides, the flow cell was hybridized again with labeled oligonucleotides. FIG. 9 also shows the imaging results for labeled anti-P5 and anti-P7 oligonucleotides (C). FIG. 9 also shows the imaging results for labeled anti-ME oligonucleotides (D).

FIG. 12 illustrates application-specific capture primers including universal capture regions (P5 and P7) and a transposon end region (ME) at their 3' end (A). Some surface primers are hybridized with a transposon end oligonucleotide (16-mer) and bind transposase. Primer-transposase complexes can dimerize to form surface transposomes. Transposon end regions of hairpin capture primers that have failed to assemble into transposomes can be removed with exonuclease I. FIG. 12 also illustrates capture primers with a secondary structure that is stable at about 38° C. (the temperature at which exonuclease I operates) but is disrupted at 60° C. (the temperature at which bridge amplification is carried out).

DETAILED DESCRIPTION

Bridge amplification is one step in next generation sequencing. Bridge amplification relies on the capture of polynucleotide templates by universal capture primers that are immobilized on a solid surface. Universal capture primers cannot target or capture specific polynucleotides based on their specific nucleic acid sequences. However, a growing number of next generation sequencing applications require the application-specific capture of application-specific polynucleotides and therefore the immobilization of application-specific capture primers besides universal capture primers on the same surface.

For example, a growing number of next generation sequencing applications require the target-specific capture of target-specific polynucleotides and therefore the immobilization of target-specific capture primers besides universal capture primers on the same surface. In another example, sequence tagmenteation applications require the presence of universal capture primers, and also the presence of application-specific capture primers that have transposon ends (TE) and hybridize with transposon end oligonucleotides.

The present disclosure is based, in part, on the realization that the presence of application-specific capture primers on a solid surface next to universal capture primers interferes with current bridge amplification protocols.

For example, the presence of target-specific capture primers next to universal capture primers interfers with bridge amplification. Direct target capture can be achieved by immobilizing target-specific capture primers on a surface that specifically hybridize with a target polynucleotide, e.g., a polynucleotide encoding a mutated oncogene. In applications where many target polynucleotides need to be captured on the same flow cell (e.g., a plurality of polynucleotides encoding known mutations in human oncogenes) the target-specific capture primers are necessarily many and varied. A high concentration of target-specific capture primers on a solid support would make target capture fast, efficient and robust. Speed, efficiency and robustness are especially important where the target polynucleotides are extremely rare and have a low abundance, for example in the case of target polynucleotides encoding somatic mutations of human oncogenes. However, if only target-specific capture primers are present on a support, effective bridge amplification cannot occur.

Figure 5:
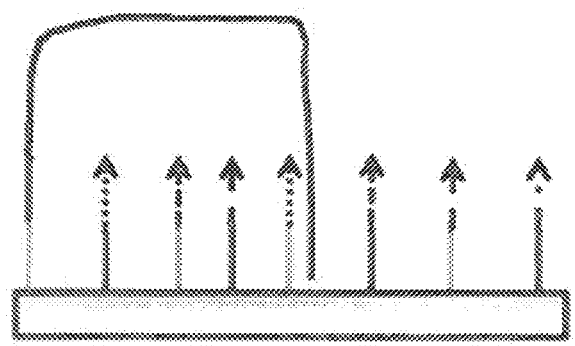
FIG. 5 is a schematic illustrating two alternative hybridization scenarios involving an immobilized target polynucleotide, and illustrates that an immobilized target polynucleotide can hybridize with a matching target-specific capture-region and support effective capture primer extension to copy the target polynucleotide.
Figure 5:
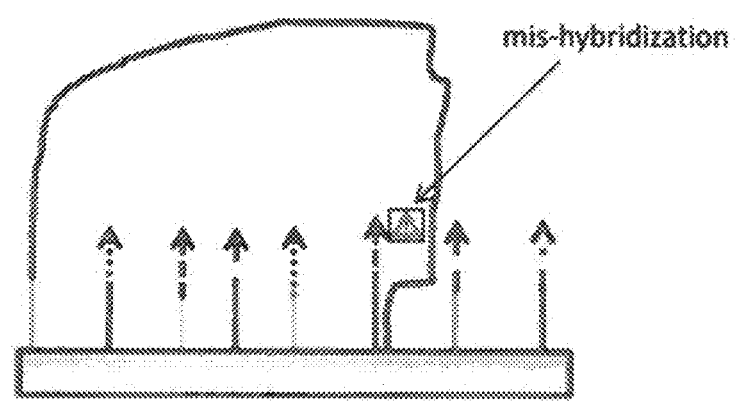

In general, only specifically captured target polynucleotides can efficiently support bridge amplification. By contrast polynucleotides that are mishybridized to a mismatched capture primer can be inefficient in supporting capture primer extension. As a result, the mismatched polynucleotide can be inefficiently copied or amplified (see, e.g., FIG. 5). Thus, if 1,000 different target polynucleotides were to be captured onto a flow cell and if all of the capture primers were target-specific capture probes, only 0.1% of the capture probes could effectively support bridge amplification of a specific target molecule, which is inefficient. Therefore, in order to ensure efficient amplification, a large excess of universal capture primers would have to be combined on the solid support with only a small number of target-specific capture primers. Moreover, it would be necessary to carefully choose a density of target-specific capture primers that is adequate to capture the target polynucleotide but not so high as to impede the subsequent amplification step.

Thus, the need to compromise between efficient target capture and efficient target amplification potentially limits the performance of direct capture applications, for example, by lowering the sensitivity of target detection. Moreover, suboptimal target capture and target amplification will increase the noise in the method's results, reduce the method's robustness and ultimately reduce the utility of direct target capture applications.

Figure 1:
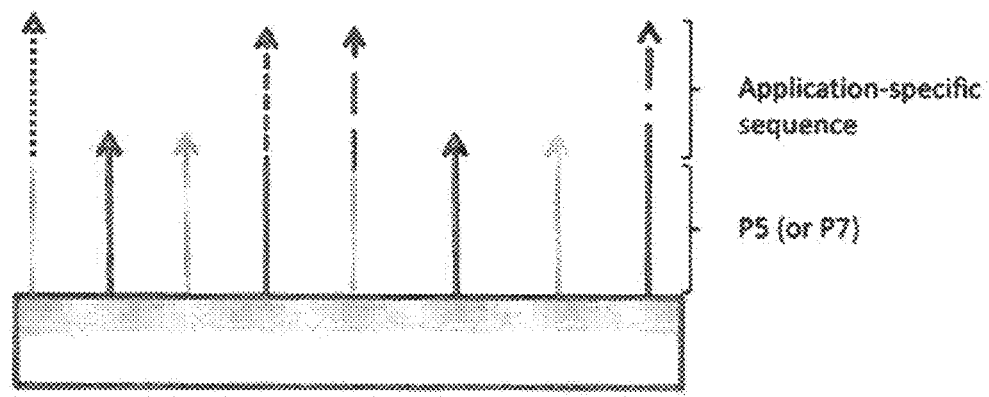
FIG. 1 is a schematic illustrating the design of application-specific capture primers and universal capture primers. Universal capture primers are represented by the universal Illumina® capture primers P5 and P7, which are shown as black arrows. application-specific capture primers are shown as extended arrows. Universal capture regions are exemplified by P5 and P7 regions, which are shown as black regions in the extended arrows. application-specific capture regions are shown as dashed lines having different patterns. In application-specific capture primers the universal capture regions are located at the 5' end of the primers in proximity to the solid support. The application-specific capture regions are located at the 3' end of the primers.

The present disclosure is further based, in part, on the realization that application-specific capture primers can be designed to include both application-specific capture regions and universal capture regions. For example, FIG. 1 illustrates that application-specific capture primers can be designed to include a universal capture region at their 5'-end (the portion closer to the solid support, shown as solid black lines) and an additional application-specific capture region at their 3'-end (shown in as dashed lines with different patterns). The nature of the application-specific capture region can vary according to the type of application the application-specific capture primer is intended for. For example, in order to capture target polynuclotides encoding oncogene mutations, the capture primer will include a target-specific capture region complementary to the targeted oncogene mutation. In another example, the application-specific capture primer can contain an application-specific capture region encoding a transposon end (TE) and mediate surface tagmentation reactions (see, e.g., FIG. 6).

Figure 2:
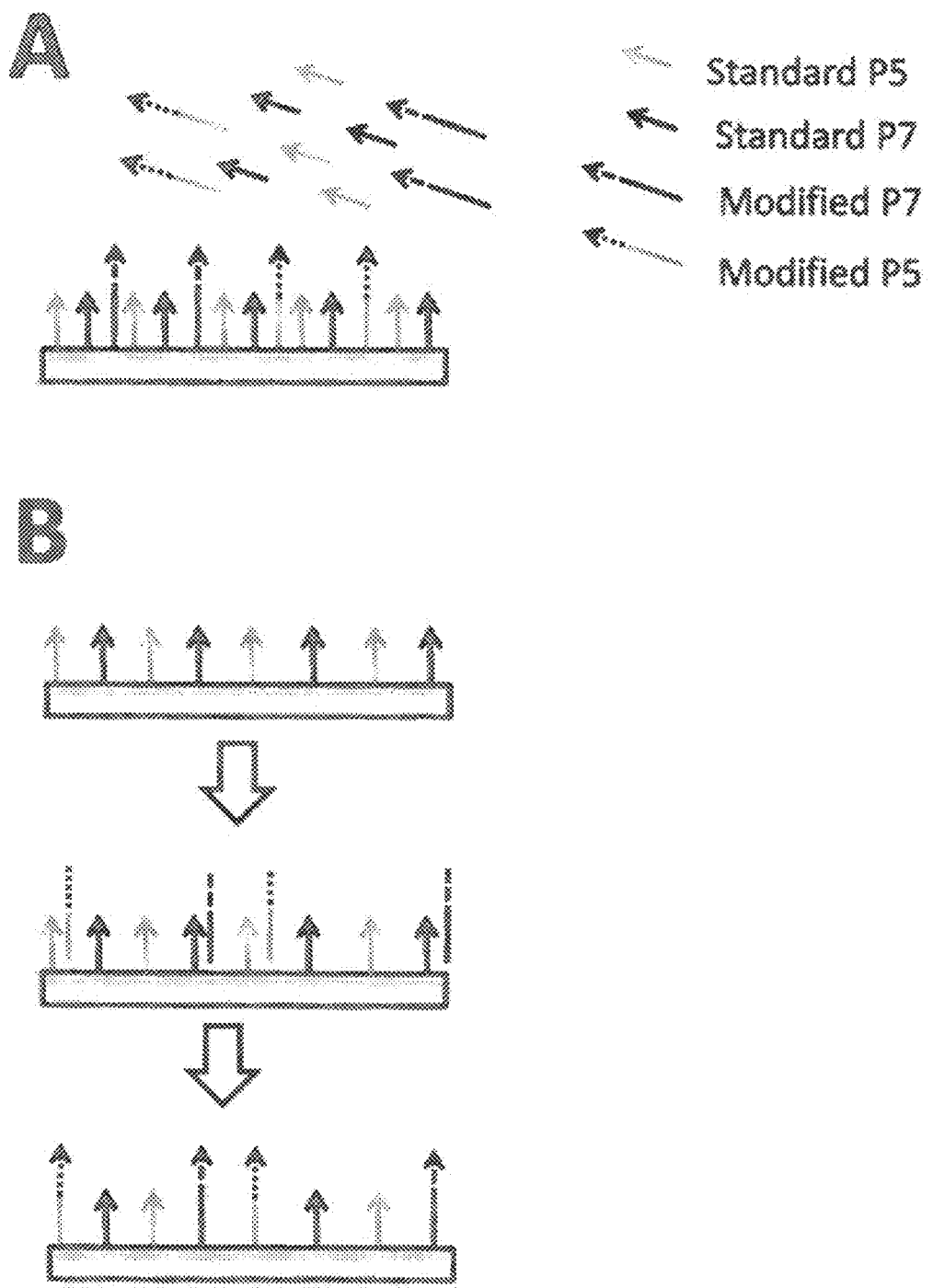
FIG. 2 is a schematic exemplifying two methods of attaching application-specific capture primers to a solid support, and exemplifies the direct immobilization of universal capture primers (referred to as "Standard P5" and "Standard P7") and application-specific capture primers (referred to as "Modified P5" and "Modified P7").

The present disclosure is further based, in part, on the realization that application-specific capture primers can be assembled on a surface in several ways (see, e.g., FIG. 2). For example, application-specific capture primers can be immobilized directly onto a solid surface (see, e.g., FIG. 2A, universal capture regions shown as solid black lines, application-specific capture regions shown as dashed lines with different patterns). In another example, the application-specific capture primers can be assembled on the solid surface, e.g., by using a primer hybridization and extension approach (see, e.g., FIG. 2B).

Figure 3:
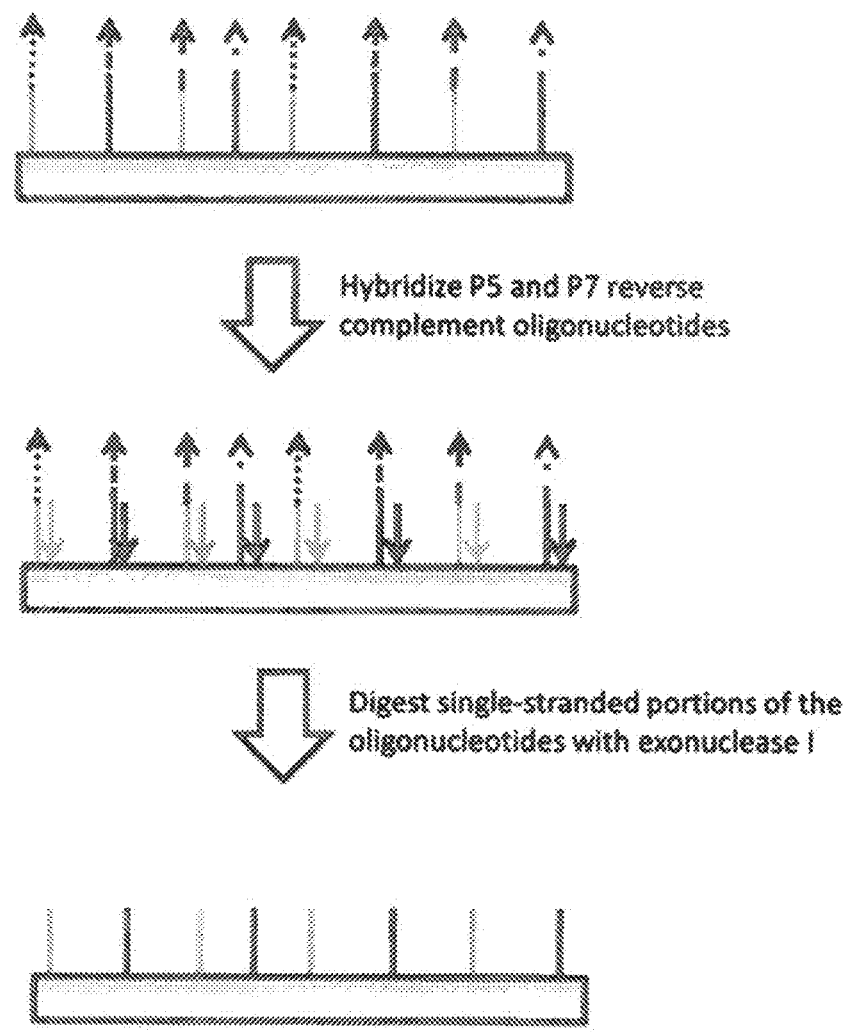
FIG. 3 is a schematic exemplifying a method of removing an application-specific capture region from an application-specific capture primer, thereby converting the application-specific capture primer to a universal capture primer.
Figure 4:
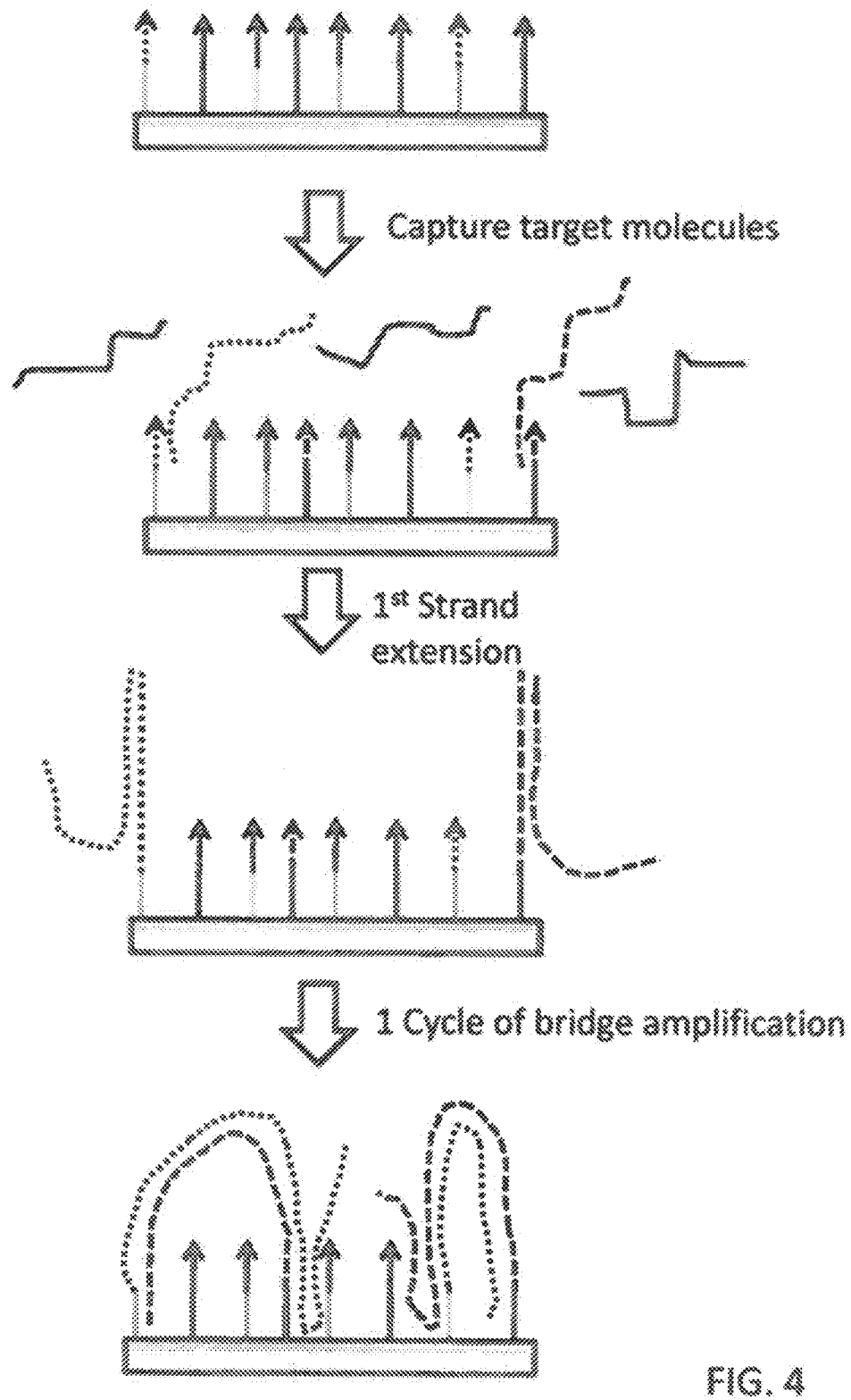
FIG. 4 is a schematic exemplifying a method of removing target-specific capture regions from capture primers in a direct target capture application.
Figure 4:
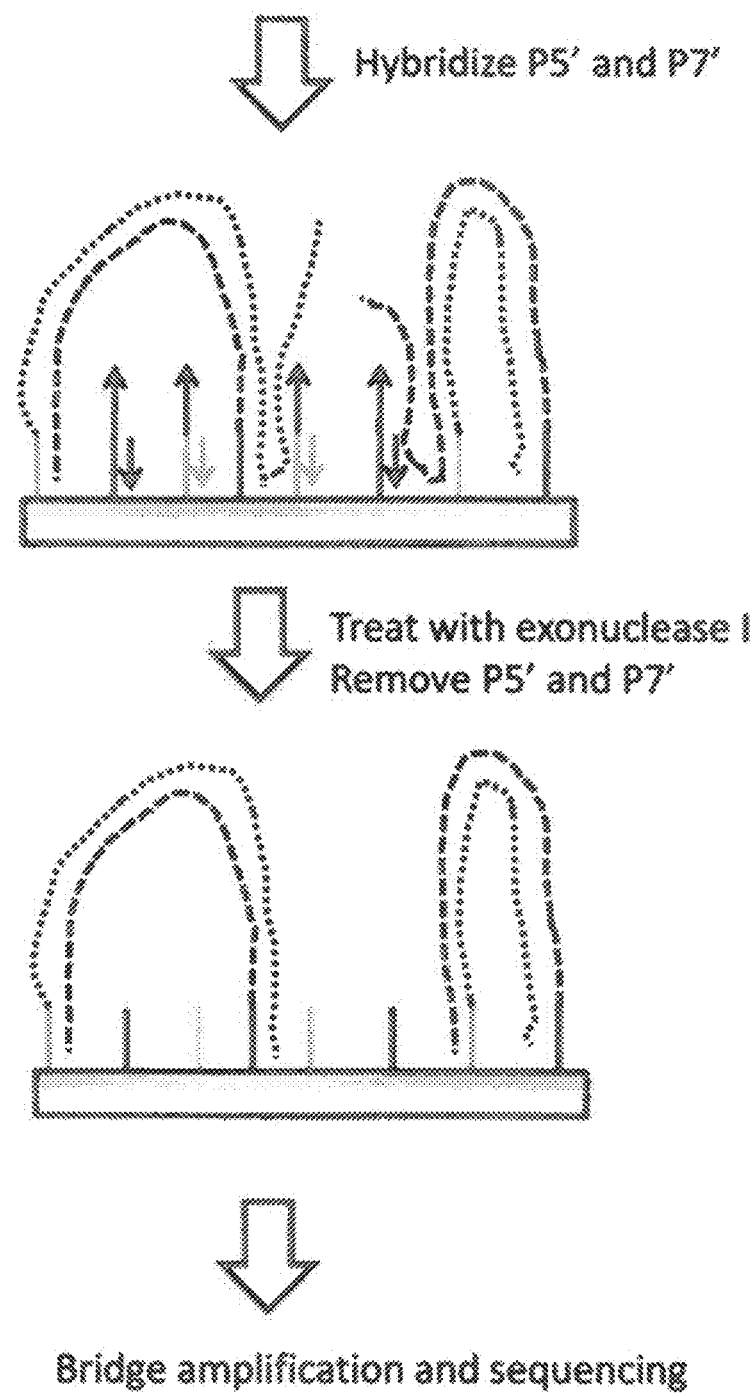
Figure 6:
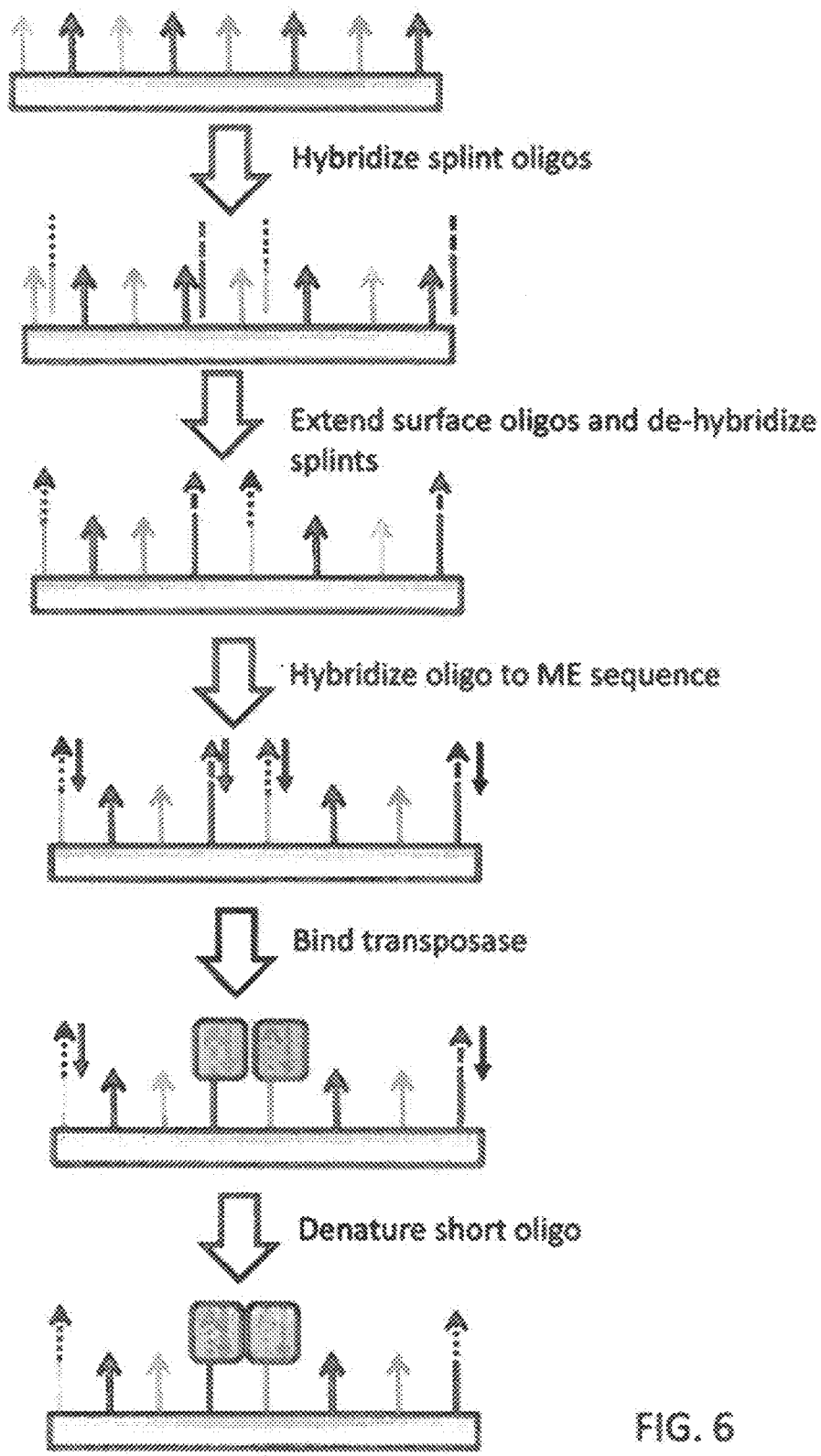
FIG. 6 is a schematic exemplifying the preparation of a flow cell for surface tagmentation.

The present disclosure relates, in part, to the surprising discovery that an application specific polynucleotide can be hybridized with an application-specific capture primer and that the application-specific region of an unhybridized application-specific capture primer can thereafter be removed to convert the unhybridized application-specific capture primer to a universal primer (see, e.g., FIGS. 3, 4, and 6).

The disclosure provides methods and kits for modifying an immobilized capture primer. One benefit of the present disclosure is that it enables the effective use of application-specific capture primers in next generation sequencing. Specifically, the present disclosure facilitates the collection of high quality data in advanced next generation sequencing applications that require the use of application-specific capture primers. High data quality opens up a wide new field of applications for target-specific next generation sequencing, e.g., in disease diagnostics and prognostication.

Moreover, the surprisingly efficient removal of application-specific capture regions from unhybridized application-specific capture primers improves both the data quality (error rate, sensitivity) and data quantity (number of clusters counted) of surface tagmentation applications. By facilitating surface tagmentation techniques in next generation sequencing, this disclosure benefits efforts to automate and streamline sample preparation and sample throughput. The methods provided herein thereby help to cut the costs of high-throughput sequencing technologies. Moreover this disclosure is expected to benefit patients suffering from diseases that involve rare genetic mutations, e.g., cancer patients, by facilitating the reliable early detection of rare genetic mutations. Earlier disease detection typically translates into a greater number of treatment options and improved treatment outcomes.

It must be noted that, as used in this specification and the appended claims, the singular forms "a", "an" and "the" include plural referents unless the content clearly dictates otherwise. Thus, for example, reference to "a biomarker" includes a mixture of two or more biomarkers, and the like.

The term "about," particularly in reference to a given quantity, is meant to encompass deviations of plus or minus five percent.

As used herein, the terms "includes," "including," "includes," "including," "contains," "containing," and any variations thereof, are intended to cover a non-exclusive inclusion, such that a process, method, product-by-process, or composition of matter that includes, includes, or contains an element or list of elements does not include only those elements but can include other elements not expressly listed or inherent to such process, method, product-by-process, or composition of matter.

As used herein, the term "plurality" refers to a population of two or more members, such as polynucleotide members or other referenced molecules. In some embodiments, the two or more members of a plurality of members are the same members. For example, a plurality of polynucleotides can include two or more polynucleotide members having the same nucleic acid sequence. In some embodiments, the two or more members of a plurality of members are different members. For example, a plurality of polynucleotides can include two or more polynucleotide members having different nucleic acid sequences. A plurality includes 2, 3, 4, 5, 6, 7, 8, 9, 10, 20, 30, 40, 50, 60, 70, 80, 90 or a 100 or more different members. A plurality can also include 200, 300, 400, 500, 1000, 5000, 10000, 50000, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$ or $1\times10^7$ or more different members. A plurality includes all integer numbers in between the above exemplary plurality numbers.

As used herein, the term "target polynucleotide" is intended to mean a polynucleotide that is the object of an analysis or action. The analysis or action includes subjecting the polynucleotide to copying, amplification, sequencing and/or other procedure for nucleic acid interrogation. A target polynucleotide can include nucleotide sequences additional to the target sequence to be analyzed. For example, a target polynucleotide can include one or more adapters, including an adapter that functions as a primer binding site, that flank(s) a target polynucleotide sequence that is to be analyzed. A target polynucleotide hybridized to a capture oligonucleotide or capture primer can contain nucleotides that extend beyond the 5' or 3' end of the capture oligonucleotide in such a way that not all of the target polynucleotide is amenable to extension. In particular embodiments, as set forth in further detail below, a plurality of target polynucleotides includes different species that differ in their target polynucleotide sequences but have adapters that are the same for two or more of the different species. The two adapters that can flank a particular target polynucleotide sequence can have the same sequence or the two adapters can have different sequences. Accordingly, a plurality of different target polynucleotides can have the same adapter sequence or two different adapter sequences at each end of the target polynucleotide sequence. Thus, species in a plurality of target polynucleotides can include regions of known sequence that flank regions of unknown sequence that are to be evaluated by, for example, sequencing. In cases where the target polynucleotides carry an adapter at a single end, the adapter can be located at either the 3' end or the 5' end the target polynucleotide. Target polynucleotides can be used without any adapter, in which case a primer binding sequence can come directly from a sequence found in the target polynucleotide.

As used herein, the term "capture primers" is intended to mean an oligonucleotide having a nucleotide sequence that is capable of specifically annealing to a single stranded polynucleotide sequence to be analyzed or subjected to a nucleic acid interrogation under conditions encountered in a primer annealing step of, for example, an amplification or sequencing reaction. Generally, the terms "nucleic acid," "polynucleotide" and "oligonucleotide" are used interchangeably herein. The different terms are not intended to denote any particular difference in size, sequence, or other property unless specifically indicated otherwise. For clarity of description the terms can be used to distinguish one species of nucleic acid from another when describing a particular method or composition that includes several nucleic acid species.

As used herein, the term "target specific" when used in reference to a capture primer or other oligonucleotide is intended to mean a capture primer or other oligonucleotide that includes a nucleotide sequence specific to a target polynucleotide sequence, namely a sequence of nucleotides capable of selectively annealing to an identifying region of a target polynucleotide. Target specific capture primers can have a single species of oligonucleotide, or it can include two or more species with different sequences. Thus, the target specific capture primers can be two or more sequences, including 3, 4, 5, 6, 7, 8, 9 or 10 or more different sequences. The target specific capture oligonucleotides can include a target specific capture primer sequence and universal capture primer sequence. Other sequences such as sequencing primer sequences and the like also can be included in a target specific capture primer.

In comparison, the term "universal" when used in reference to a capture primer or other oligonucleotide sequence is intended to mean a capture primer or other oligonucleotide having a common nucleotide sequence among a plurality of capture primers. A common sequence can be, for example, a sequence complementary to the same adapter sequence. Universal capture primers are applicable for interrogating a plurality of different polynucleotides without necessarily distinguishing the different species whereas target specific capture primers are applicable for distinguishing the different species.

As used herein, the term "immobilized" when used in reference to a nucleic acid is intended to mean direct or indirect attachment to a solid support via covalent or non-covalent bond(s). In certain embodiments of the invention, covalent attachment can be used, but generally all that is required is that the nucleic acids remain stationary or attached to a support under conditions in which it is intended to use the support, for example, in applications requiring nucleic acid amplification and/or sequencing. Typically, oligonucleotides to be used as capture primers or amplification primers are immobilized such that a 3' end is available for enzymatic extension and at least a portion of the sequence is capable of hybridizing to a complementary sequence. Immobilization can occur via hybridization to a surface attached oligonucleotide, in which case the immobilised oligonucleotide or polynucleotide can be in the 3'-5' orientation. Alternatively, immobilization can occur by means other than base-pairing hybridization, such as the covalent attachment set forth above.

As used herein, the term "transposome complex" refers generally to a transposase enzyme non-covalently bound to a double stranded nucleic acid. For example, the complex can be a transposase enzyme preincubated with double-stranded transposon DNA under conditions that support non-covalent complex formation. Double-stranded transposon DNA can include, without limitation, Tn5 DNA, a portion of Tn5 DNA, a transposon end composition, a mixture of transposon end compositions or other double-stranded DNAs capable of interacting with a transposase such as the hyperactive Tn5 transposase.

A "transposase" means an enzyme that is capable of forming a functional complex with a transposon end-containing composition (e.g., transposons, transposon ends, transposon end compositions) and catalyzing insertion or transposition of the transposon end-containing composition into the double-stranded target DNA with which it is incubated, for example, in an in vitro transposition reaction. A transposase as presented herein can also include integrases from retrotransposons and retroviruses. Transposases, transposomes and transposome complexes are generally known to those of skill in the art, as exemplified by the disclosure of US 2010/0120098, the content of which is incorporated herein by reference in its entirety. Although many embodiments described herein refer to Tn5 transposase and/or hyperactive Tn5 transposase, it will be appreciated that any transposition system that is capable of inserting a transposon end with sufficient efficiency to 5'-tag and fragment a target DNA for its intended purpose can be used in the present invention. In particular embodiments, a preferred transposition system is capable of inserting the transposon end in a random or in an almost random manner to 5'-tag and fragment the target DNA.

The term "transposon end" (TE) refers to a double-stranded nucleic acid DNA that exhibits only the nucleotide sequences (the "transposon end sequences") that are necessary to form the complex with the transposase or integrase enzyme that is functional in an in vitro transposition reaction. In some embodiments, a transposon end is capable of forming a functional complex with the transposase in a transposition reaction. As non-limiting examples, transposon ends can include the 19-bp outer end ("OE") transposon end, inner end ("IE") transposon end, or "mosaic end" ("ME") transposon end recognized by a wild-type or mutant Tn5 transposase, or the R1 and R2 transposon end as set forth in the disclosure of US 2010/0120098, the content of which is incorporated herein by reference in its entirety. Transposon ends can include any nucleic acid or nucleic acid analogue suitable for forming a functional complex with the transposase or integrase enzyme in an in vitro transposition reaction. For example, the transposon end can include DNA, RNA, modified bases, non-natural bases, modified backbone, and can include nicks in one or both strands. Although the term "DNA" is used throughout the present disclosure in connection with the composition of transposon ends, it should be understood that any suitable nucleic acid or nucleic acid analogue can be utilized in a transposon end.

The term "transposon end oligonucleotide" (TEO) or "transposon end region" (TER), as used herein, refers to a single stranded nucleic acid DNA that includes a transposon end sequence.

The term "transferred strand" refers to the transferred portion of both transposon ends. Similarly, the term "non-transferred strand" refers to the non-transferred portion of both "transposon ends." The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction.

In some embodiments, the transferred strand and non-transferred strand are covalently joined. For example, in some embodiments, the transferred and non-transferred strand sequences are provided on a single oligonucleotide, e.g., in a hairpin configuration. As such, although the free end of the non-transferred strand is not joined to the target DNA directly by the transposition reaction, the non-transferred strand becomes attached to the DNA fragment indirectly, because the non-transferred strand is linked to the transferred strand by the loop of the hairpin structure. Additional examples of transposome structure and methods of preparing and using transposomes can be found in the disclosure of US 2010/0120098, the content of which is incorporated herein by reference in its entirety.

In the methods and compositions presented herein, capture primers are immobilized to the solid support. In some embodiments, the capture primers can be immobilized via a linker molecule coupling the capture primers to the solid support. When referring to immobilization of molecules (e.g., nucleic acids) to a solid support, the terms "immobilized" and "attached" are used interchangeably herein and both terms are intended to encompass direct or indirect, covalent or non-covalent attachment, unless indicated otherwise, either explicitly or by context. In certain embodiments of the invention covalent attachment is preferred, but generally all that is required is that the molecules (e.g., nucleic acids) remain immobilized or attached to the support under the conditions in which it is intended to use the support, for example in applications requiring nucleic acid amplification and/or sequencing.

Certain embodiments of the invention can make use of solid supports included of an inert substrate or matrix (e.g., glass slides, polymer beads etc.) which has been functionalized, for example, by application of a layer or coating of an intermediate material including reactive groups which permit covalent attachment to biomolecules, such as polynucleotides. Examples of such supports include, but are not limited to, polyacrylamide hydrogels supported on an inert substrate such as glass, particularly polyacrylamide hydrogels as described in WO 2005/065814 and US 2008/0280773, the contents of which are incorporated herein in their entirety by reference. In such embodiments, the biomolecules (e.g., polynucleotides) can be directly covalently attached to the intermediate material (e.g., the hydrogel) but the intermediate material can itself be non-covalently attached to the substrate or matrix (e.g., the glass substrate). The term "covalent attachment to a solid support" is to be interpreted accordingly as encompassing this type of arrangement.

The terms "solid surface," "solid support" and other grammatical equivalents herein refer to any material that is appropriate for or can be modified to be appropriate for the attachment of the transposome complexes. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. Particularly useful solid supports and solid surfaces for some embodiments are located within a flow cell apparatus. Exemplary flow cells are set forth in further detail below.

In some embodiments, the solid support includes a patterned surface suitable for immobilization of capture primers in an ordered pattern. A "patterned surface" refers to an arrangement of different regions in or on an exposed layer of a solid support. For example, one or more of the regions can be features where one or more capture primers are present. The features can be separated by interstitial regions where capture primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. In some embodiments, the capture primers are randomly distributed upon the solid support. In some embodiments, the capture primers are distributed on a patterned surface. Exemplary patterned surfaces that can be used in the methods and compositions set forth herein are described in U.S. Ser. No. 13/661,524 or US Pat. App. Publ. No. 2012/0316086 A1, each of which is incorporated herein by reference.

In some embodiments, the solid support includes an array of wells or depressions in a surface. This can be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The composition and geometry of the solid support can vary with its use. In some embodiments, the solid support is a planar structure such as a slide, chip, microchip and/or array. As such, the surface of a substrate can be in the form of a planar layer. In some embodiments, the solid support includes one or more surfaces of a flowcell. The term "flowcell" as used herein refers to a chamber including a solid surface across which one or more fluid reagents can be flowed. Examples of flowcells and related fluidic systems and detection platforms that can be readily used in the methods of the present disclosure are described, for example, in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

In some embodiments, the solid support or its surface is non-planar, such as the inner or outer surface of a tube or vessel. In some embodiments, the solid support includes microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and teflon, as well as any other materials outlined herein for solid supports can all be used. "Microsphere Detection Guide" from Bangs Laboratories, Fishers Ind. is a helpful guide. In certain embodiments, the microspheres are magnetic microspheres or beads.

The beads need not be spherical; irregular particles can be used. Alternatively or additionally, the beads can be porous. The bead sizes range from nanometers, e.g., 100 nm, to millimeters, e.g. 1 mm, with beads from about 0.2 micron to about 200 microns being preferred, and from about 0.5 to about 5 micron being particularly preferred, although in some embodiments smaller or larger beads can be used.

Provided herein are methods of modifying an immobilized capture primer, including a) providing a solid support having an immobilized application-specific capture primer, the application-specific capture primer including i) a 3' portion including an application-specific capture region, and ii) a 5' portion including a universal capture region; b) contacting an application-specific polynucleotide with the application-specific capture primer under conditions sufficient for hybridization to produce an immobilized application-specific polynucleotide; and c) removing the application-specific capture region of an application-specific capture primer not hybridized to an application-specific polynucleotide to convert the unhybridized application-specific capture primer to a universal capture primer.

In one aspect, this disclosure provides a method of modifying an immobilized capture primer including: a) providing a solid support having an immobilized application-specific capture primer, said application-specific capture primer including: i) a 3' portion including a target-specific capture region, and ii) a 5' portion including a universal capture region; b) contacting a target polynucleotide with the application-specific capture primer under conditions sufficient for hybridization to produce an immobilized target-specific polynucleotide; c) extending a hybridized application-specific capture primer to produce an immobilized extension product complementary to an immobilized target-specific polynucleotide; d) applying an oligonucleotide under conditions sufficient for the oligonucleotide to hybridize with the universal capture region of the immobilized application-specific capture primer; e) contacting the immobilized application-specific capture primer with nuclease under conditions sufficient for the nuclease to remove the target-specific capture region of an application-specific capture primer not hybridized to the target polynucleotide to convert the unhybridized application-specific capture primer to a universal capture primer; e) removing the oligonucleotide from the immobilized application-specific capture primer; g) annealing the universal capture primer to the immobilized extension products; h) amplifying by PCR the immobilized extension product to produce a plurality of immobilized amplicons, and i) sequencing the plurality of immobilized amplicons, wherein sequencing comprises a bridge amplification step.

In another aspect, this disclosure provides a method of modifying an immobilized polynucleotide capture primer including: a) providing a solid support having an immobilized application-specific capture primer, said application-specific capture primer including: i) a 3' portion including a transposon end (TE) region, and ii) a 5' portion including a universal capture region; b) contacting a transposon end oligonucleotide (TEO) with the application-specific capture primer under conditions sufficient for hybridization to produce an immobilized TE region—TEO hybrid; c) binding a transposase to the TE region—TEO hybrid to produce a support bound transposome complexe; d) contacting the support bound transposome complexe with a target polynucleotide under conditions wherein the support-bound transposome complex joins the 3'-end of the TE region in the application-specific capture primer (the "transferred strand") to the target polynucleotide to produce an immobilized target polynucleotide; e) removing the transposase and the TEO from the solid support; g) extending the 3'-ends of the immobilized target polynucleotide; h) applying an oligonucleotide under conditions sufficient for the oligonucleotide to hybridize with the universal capture region in the immobilized application-specific capture primer; i) contacting the application-specific capture primer with nuclease under conditions sufficient for the nuclease to remove the TE region of an application-specific capture primer not hybridized to the TEO to convert the application-specific capture primer to a universal capture primer; j) removing the oligonucleotide from the universal capture primer; k) amplifying by PCR the immobilized target polynucleotide to produce a plurality of immobilized amplicons; l) sequencing the plurality of immobilized amplicons, wherein sequencing comprises a bridge amplification step.

In some embodiments, the application-specific capture region includes a target-specific capture region and the application-specific polynucleotide includes a target polynucleotide.

In some embodiments, the application-specific capture region includes a transposon end (TE) region and the application-specific polynucleotide includes a TE oligonucleotide.

In some embodiments, the methods of this disclosure further include applying an oligonucleotide before execution of step c) under conditions sufficient for oligonucleotide hybridization with the universal capture region of an application-specific capture primer to produce a double-stranded DNA region. In certain embodiments, the oligonucleotide is applied before execution of step b), e.g., before production of the immobilized application-specific polynucleotide. In certain other embodiments, the oligonucleotide is applied after completion of step b), e.g., after production of the immobilized target-specific polynucleotide.

In certain embodiments, the oligonucleotide can hybridize with an Illumina® capture primer P5 (5'- AATGATACGGCGACCACCGA-3') or P7 (5'-CAAGCAGAAGACGGCATACGA-3'). In certain embodiments, the oligonucleotide is the reverse complement of the Illumina® capture primer P5 ("anti-P5": 5'-TCGGTGGTCGCCGTATCATT-3') or P7 ("anti-P7": 5'-TCGTATGCCGTCTTCTGCTTG-3'). In certain embodiments, the oligonucleotide can hybridize with Illumina® capture primers P5 (paired end) (5'-AATGATACGGCGACCACCGAGAUCTACAC-3') or P7 (paired end) (5'-CAAGCAGAAGACGGCATACGA (8-oxo-G)AT-3'). In certain embodiments, the oligonucleotide can hybridize with the reverse complement of the Illumina® capture primer P5 (paired end) ("anti-P5 (paired end)": 5'-GTGTAGATCTCGGTGGTCGCCGTATCATT-3') or P7 (paired end) ("anti-P7 (paired end)": 5'-ATCTCGTATGCCGTCTTCTGCTTG-3').

The capture primers of this disclosure can be universal capture primers or application-specific capture primers. In some embodiments, the universal capture primers include a known sequence. In certain embodiments the known sequence is the sequence of the Illumina® capture primers P5 and P7 (see, e.g., FIG. 1; universal capture primers shown as black arrows).

Application-specific capture primers include i) a 3' portion including an application-specific capture region, and ii) a 5' portion including a universal capture region (see, e.g., FIG. 1; the universal capture regions are exemplified by P5 and P7 regions, shown as solid black lines; the application-specific capture regions are shown as dashed lines with different patterns). The application-specific capture primers of this disclosure hybridize with an application-specific polynucleotide. In some embodiments, the application-specific polynucleotide is a transposon end (TE) oligonucleotide (TEO; e.g., a mosaic end oligonucleotide (MEO)). In some embodiments, the application-specific polynucleotide is a target polynucleotide. In some embodiments, the target polynucleotide is in its wild-type form. In other embodiments the target polynucleotide is in its mutant form. In some embodiments, the target polynucleotide encodes a polypeptide. In some embodiments, the target polynucleotide encodes an oncogene. In some embodiments, the target polynucleotide encodes a biomarker (e.g., a disease marker).

Figure 12:
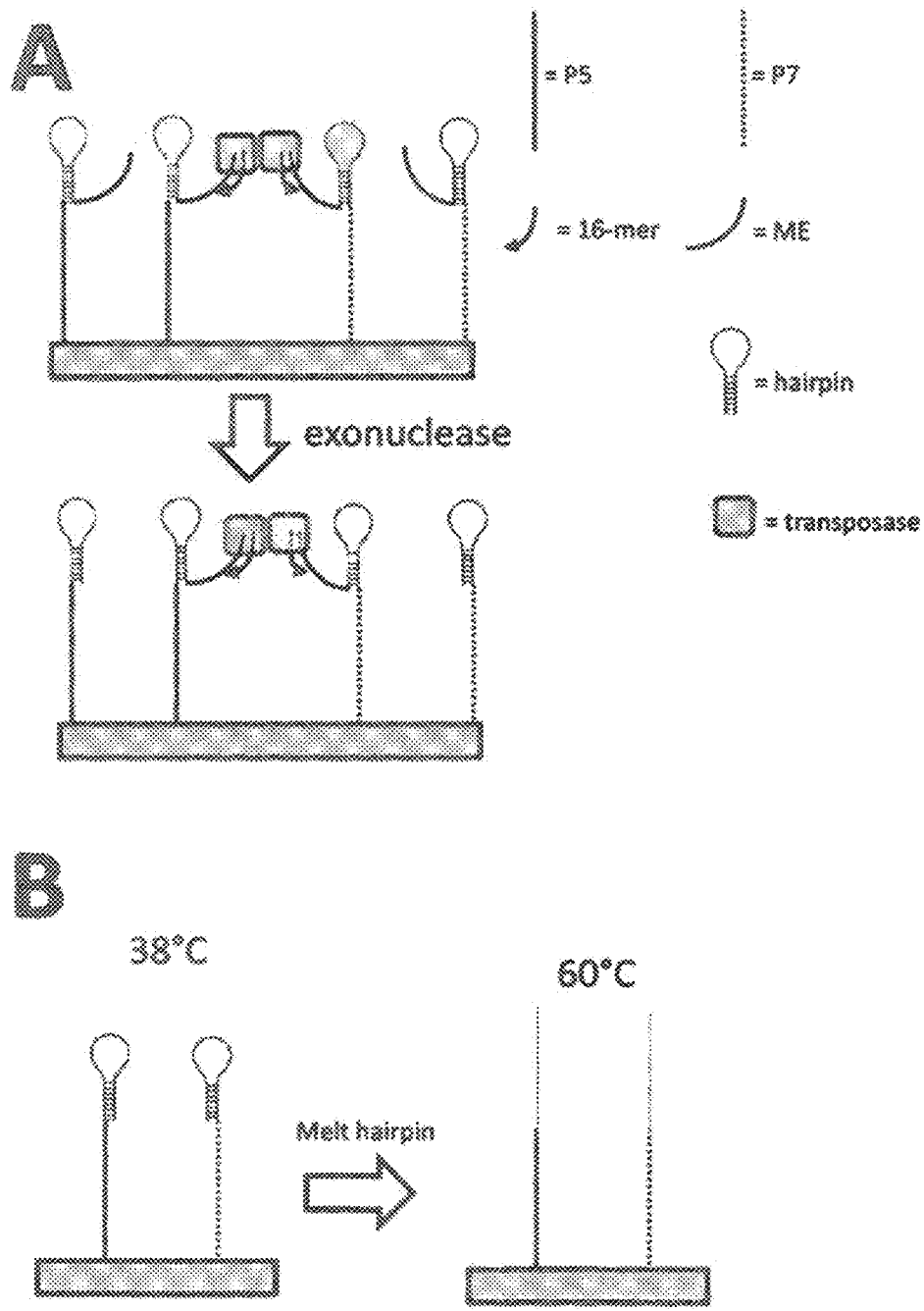
FIG. 12 is a schematic illustrating surface primers with a hairpin structure that are self-protecting against the activity of exonuclease I.

In some embodiments, the capture primer has a hairpin structure (see, e.g., FIG. 12).

In some embodiments, the methods of this disclosure include providing a solid support having an immobilized application-specific capture primer. In some embodiments, providing solid support includes immobilizing the application-specific capture primer onto the solid support FIGS. 2A and 2B generally illustrate one configuration for how the application-specific capture primers can be immobilized.

In some embodiments, the application-specific capture primer is immobilized directly onto the solid support. For purposes of these embodiments, "directly" means that the application-specific capture primer was synthesized prior to its immobilization as opposed to being assembled from different parts on the solid support.

FIG. 2A illustrates generally how, according to one embodiment, an application-specific capture primer (referred to as "Modified P7" and "Modified P5" in FIG. 2A) can be immobilized directly onto the surface (universal capture regions are shown as solid black lines, application-specific capture regions are shown as dashed lines in different patterns).

In some embodiments, the application-specific capture primer is assembled on the solid support in one or more steps. In some embodiments, the immobilization of an application-specific capture primer includes immobilizing a universal capture primer onto the solid support. In certain embodiments, the method further includes converting the immobilized universal capture primer into the application-specific capture primer. In certain embodiments, the method further includes annealing a splint oligonucleotide with the universal capture primer, wherein the splint oligonucleotide includes a universal region complementary to a universal region of an application-specific capture primer and an application-specific region complementary to an application-specific region in an application-specific nucleotide. In certain embodiments, the method further includes extending the universal capture primer to produce an application-specific capture primer.

FIG. 2B illustrates generally how, according to one embodiment, a solid support such as a flowcell, can be modified to assemble an application-specific capture primer using the primer hybridization and extension method (universal capture regions are shown as black lines; application-specific capture regions are shown as dashed lines in different patterns).

In some embodiments, the application-specific capture primer is immobilized in combination with other application-specific capture primers. In some embodiments, the application-specific capture primer includes a plurality of application-specific capture primers. In some embodiments, the applications-specific capture primers in the plurality of application-specific capture primers are the same application-specific capture primers. In some embodiments, the application-specific capture primers in the plurality of application-specific capture primers are different application-specific capture primers.

In some embodiments, the application-specific capture primers in the plurality of application-specific capture primers have the same universal capture regions. In some embodiments, the application-specific capture primers in the plurality of application-specific capture primers have different universal capture regions.

In some embodiments, the application-specific capture primers in the plurality of application-specific capture primers have the same application-specific capture regions. In some embodiments, the application-specific capture primers in the plurality of application-specific capture primers have different application-specific capture regions.

In some embodiments, the plurality of application-specific capture primers includes only one member. In some embodiments, the one application-specific capture primers includes a universal capture region and a target-specific capture region. In some embodiments, the one application-specific capture primer includes a universal capture region and a transposon end sequence.

In some embodiments, the plurality of application-specific capture primers includes two different application-specific capture primers. In some embodiments, each application-specific capture primers includes one of two universal capture regions, e.g., P5 or P7 regions, and each contains the same application-specific region. In some embodiments, the same application-specific region is a target-specific capture region. In some embodiments, the same application-specific region is a target- end region.

In some embodiments the plurality of application-specific capture primers includes more than two different application-specific capture primers. In some embodiments, the application-specific capture primers in the plurality of application-specific capture primers each include the same universal capture region, e.g., a P5 or P7 region, and each include a different application-specific capture region. In some embodiments, the application-specific capture primers in the plurality of application-specific capture primers each include one of two universal capture regions, e.g., P5 or P7 regions, and each include a different appication-specific capture region. In some embodiments, the application-specific capture primers in the plurality of application-specific capture primers each include one of two or more universal capture regions, e.g., P5 or P7 regions, and each include a different application-specific capture region. In some embodiments, the plurality of application-specific capture primers having different application-specific capture regions can include more than 10, 100, 1,000, 10,000, 100,000, 1,000,000 or 10,000,000 different members. In some embodiments, the different application-specific capture regions are target-specific capture regions. In some embodiments, the different application-specific capture regions are transposon end regions.

In some embodiments, the application-specific polynucleotide is a plurality of application-specific polynucleotides. In some embodiments, the application-specific polynucleotides in the plurality of application-specific polynucleotides are the same application-specific polynucleotides. In some embodiments, the application-specific polynucleotides in the plurality of application-specific polynucleotides are different application-specific polynucleotides.

In some embodiments, the target polynucleotide is a plurality of target polynucleotides. In some embodiments, the target polynucleotides in the plurality of target polynucleotides are the same target polynucleotides. In some embodiments, the target polynucleotides in the plurality of target nucleotides are different target polynucleotides.

In some embodiments, the target polynucleotides include regions that are conserved between a plurality of different target polynucleotides. In some embodiments, the plurality of different target polynucleotides includes members of a gene family (e.g., HLA gene family). In some embodiments, the plurality of different target polynucleotides include a plurality of mutated variants of a disease marker. In some embodiments, the plurality of different target polynucleotides include a plurality of mutated variants of a gene, e.g., an oncogene.

In some embodiments, the transposon end oligonucleotides are a plurality of transposon end oligonucleotides. In some embodiments, the transposon end oligonucleotides in the plurality of transposon end oligonucleotides are the same transposon end oligonucleotides. In some embodiments, the transposon end oligonucleotides in the plurality of transposon end oligonucleotides are different transposon end oligonucleotides.

In some embodiments of this disclosure, the immobilized application-specific capture primer includes a plurality of immobilized application-specific capture primers. In some embodiments, the application-specific polynucleotide includes a plurality of application-specific polynucleotides. In some embodiments, the plurality of application-specific polynucleotides includes a plurality of target polynucleotides. In some embodiments, the plurality of application-specific polynucleotides includes a plurality of TE-regions.

In some embodiments, essentially all immobilized capture primers are application-specific capture primers. In other embodiments, an application-specific capture primer is immobilized in combination with a universal capture primer. In some embodiments, an excess of application-specific capture primers is immobilized. In some embodiments, the excess of application-specific capture primers over universal capture primers is greater than 2:1, 3:1, 5:1, 10:1, 50:1, 100:1, 500:1, 1,000:1, 10,000:1, 50:000:1 or 100,000:1. In some embodiments, an excess of universal capture primers is immobilized. In some embodiments, the excess of universal capture primers over application-specific capture primers is greater than 2:1, 3:1, 5:1, 10:1, 50:1, 100:1, 500:1, 1,000:1, 10,000:1, 50:000:1 or 100,000:1.

The methods of this disclosure include removing some or all of the application-specific capture region of an unhybridized application-specific capture primer. The application-specific capture region can be removed by any chemical method (e.g., using a metal-organic complex), biochemical method (e.g., using an enzyme), or physical method (e.g., using radiation, atomic force tweezers, optical tweezers) or any method known in the art for the removal of a single-stranded unhybridized oligonucleotide or polynucleotide portion from a larger oligonucleotide or polynucleotide.

In some embodiments, the application-specific capture region is removed by a biomolecule. Biomolecules of this disclosure include, without limitation, enzymes, antibodies (e.g., catalytic antibodies) or aptamers.

In some embodiments, the biomolecule is a nuclease. In some embodiments, the nuclease is an exonuclease. The exonuclease can be a 5' to 3' exonuclease, a 3' to 5' exonuclease, or poly(A)-specific 3' to 5' exonuclease. The exonuclease can include any protein or a protein domain having exonuclease activity, e.g., DNA polymerase I. In certain embodiments, the exonuclease is exonuclease I. In certain embodiments, the exonuclease is exonuclease II. In certain embodiments, the exonuclease is exonuclease III. In certain embodiments, the exonuclease is exonuclease IV. In certain embodiments, the exonuclease is exonuclease V.

In some embodiments, the nuclease is an endonuclease. In certain embodiments, the endonuclease is a restriction endonuclease. The restriction endonuclease can be a Type I enzyme (EC 3.1.21.3), a Type II enzyme (EC 3.1.21.4), a Type III enzyme (EC 3.1.21.5), or a Type IV enzyme (EC 3.1.21.5). Restriction endonucleases can include, for example, without limitation, Alu I, Ava I, Bam HI, Bgl II, Eco P15 I, Eco RI, Eco RH, Eco RV, Hae III, Hga I, Hha I, Hind III, Hinf I, Hpa I, Kpn I, Mbo I, Not I, Pst I, Pvu II, Sac I, Sal I, Sau 3A, Sca I, Sma I, Spe I, Sph I, Sst I, Stu I, Taq I, Xba I or Xma I. The restriction endonuclease can be a recombinant restriction enzyme. Recombinant restriction enzymes can include, without limitation, fusion proteins including a natural or engineered DNA binding domain (e.g., zink finger domains, TAL effector domains) and a nuclease domain (e.g., the cleavage domain of the Type IIS restriction enzyme Fokl).

The biomolecule can be derived from any organism expressing the respective biomolecule, including eukaryotes (e.g., plants, insects, mammals) and prokaryotes. In certain embodiments the biomolecule is derived from eubacteria (e.g., gram positive, gram negative), archaebacteria, yeast, fungi, algea. Prokaryotes can include, for example, without limitation *Arthrobacter luteus, Anabaena variabilis, Bacillus amyloliquefaciens, Bacillus globigii, Escherichia coli* RY 13, *Escherichia coli* R245, *Haemophilus aegyptius, Haemophilus haemolyticus, Haemophilus inflenzae* Rd, *Haemophilus gallinarum, Haemophilus parainflenzae, Klebsiella pneumonia, Moraxella bovis, Nocardia otitidis, Proteus vulgaris, Providencia stuartii, Serratia marcescens, Sphaerotilus natans, Staphylococcus aureus, Streptomyces achromogenes, Streptomyces albus* G, *Streptomyces caespitosus, Streptomyces stanford, Streptomyces tubercidicus, Streptomyces phaeochromogenes, Thermophilus aquaticus, Xanthomonas badrii* or *Xanthamonas malvacearum*.

The biomolecule can be a wild type or a mutant form. The biomolecule can be a recombinant biomolecule.

In some embodiments, the method further includes contacting the application-specific capture primer with a nuclease, wherein the application-specific capture region is removed by the nuclease. In some embodiments, the method further includes contacting the application-specific capture primer with a nuclease, wherein the application-specific capture primer has a target-specific capture region and the target-specific capture region is removed by the nuclease.

In some embodiments, the nuclease is an exonuclease. In some embodiments, the exonuclease is exonuclease I.

FIG. 3 generally illustrates an embodiment of this disclosure (see also Example I). The top panel shows application-specific capture primers immobilized to a solid support. The application-specific capture primers contain a universal capture region proximal to the surface ("P5" or "P7", shown as solid black lines). An application-specific capture region is present at the 3' end of the capture primers (shown as dashed arrows with different patterns). In some embodiments, the application-specific capture region is a target-specific capture region. The application-specific capture region can hybridize with an application-specific polynucleotide (e.g., a transposon end oligonucleotide (TEO)) or a target polynucleotide, such as a genomic DNA fragment). According to the method of FIG. 3 the universal capture regions of the application-specific capture primers are hybridized with complementary oligonucleotides (e.g., "anti-PS" or "anti-P7") to form a double-stranded DNA segment. The application-specific region of the capture primer remains unhybridized (e.g., single-stranded) and is removed with exonuclease I. Removal of the application-specific region converts the application-specific capture primer into a universal capture primer.

In some embodiments, the methods of this disclosure further include applying an oligonucleotide before execution of step c) under conditions sufficient for oligonucleotide hybridization with the target-specific capture region of an application-specific capture primer to produce a double-stranded DNA region. In certain embodiments, the oligonucleotide is applied before execution of step b), e.g., before production of the immobilized application-specific polynucleotide. In certain other embodiments, the oligonucleotide is applied after completion of step b), e.g., after production of the immobilized target-specific polynucleotide. In some embodiments, the methods further comprise contacting the application-specific capture primer with a nuclease, wherein the double-stranded DNA is removed by the nuclease. In certain embodiments, the nuclease is exonuclease III. In certain embodiments the oligonucleotide hybridizes with a transposon end region. In certain embodiments, the oligonucleotide hybridizes with a target-specific capture region. In certain embodiments, the oligonucleotide is a plurality of oligonucleotides. In certain embodiments, the plurality of oligonucleotides hybridizes with some or all target-specific capture regions of application-specific capture primers that are immobilized on a solid support (e.g., more than 1%, 2%, 3%, 4%, 5%, 6%, 7%, 8%, 9%, 10%, 15%, 20%, 30%, 40%, 50%, 60%, 70%, 80%, 90%, 95% or 99%).

In the methods of this disclosure, removal of the application-specific capture region can include removal of some or all of the application-specific capture region. In some embodiments, all of the application-specific capture region is removed (100%). In some embodiments, less than 5%, 10%, 20%, 30%, 50%, 60%, 70%, 80%, 90%, 95% or 99% of the application-specific capture region is removed.

In some embodiments, the methods further include removing some or all of the universal capture region. In some embodiments, all of the universal capture region is removed (100%). In some embodiments, less than 5%, 10%, 20%, 30%, 50%, 60%, 70%, 80%, 90%, 95% or 99% of the universal capture region is removed. In some embodiments, the methods include contacting the application-specific capture primer with a nuclease, wherein the universal capture region is removed by the nuclease. In certain embodiments, the nuclease is exonuclease I. In certain embodiments, the nuclease is exonuclease III.

In some embodiments, the application-specific capture primer further comprises a portion including a restriction site. Restriction sites can be cleaved by restriction endonucleases. In certain embodiments, the restriction site is 4-8 base pairs in length. In certain embodiments, the restriction site is a palindromic sequence (e.g., GAATTC, the restriction site cleaved by EcoRI). In certain embodiments, the restriction site is located between the application-specific capture region and the universal capture region of an application-specific capture primer.

In some embodiments, the methods further include contacting the application-specific capture primer with a restriction endonuclease, wherein the application-specific capture primer includes a restriction site. In some embodiments, the restriction endonuclease cleaves the restriction site. In some embodiments, the restriction endonuclease removes the application-specific region of the application-specific capture primer.

In some embodiments, the application-specific capture regions are removed from essentially some or all immobilized application-specific capture primers. In some embodiments, the application-specific capture regions are removed from more than 5%, 10%, 20%, 30%, 40%, 50%, 60%, 70%, 80%, 90%, 95%, or 99% of immobilized application-specific capture primers. In some embodiments, essentially all immobilized capture primers are application-specific capture primers and the application-specific capture regions are removed from essentially all application-specific capture primers. In some embodiments, essentially all application-specific capture primers are converted to universal capture primers.

In some embodiments, the methods of this disclosure are used in target capture applications. FIG. 4 generally illustrates a use in direct target capture. The top panel shows a flowcell suitable for target capture. In this flowcell, all application-specific capture primers have a target-specific capture region at their 3' end. Each capture primer shown targets a different target polynucleotide (as indicated by dashed lines with different patterns at the 3' ends). A plurality of target polynucleotides, e.g., fragmented genomic DNA, is flowed inside the flow cell. The target polynucleotides are captured by matching target-specific capture primers. Polynucleotides that are not a target are washed away. A first round of DNA polymerization follows, ($1^{st}$ strand extension), whereby the target molecules are copied and converted from single-stranded target polynucleotides into double-stranded DNA. In some embodiments, a first cycle of bridge amplification follows (as shown, e.g., in FIG. 4). Anti-5 and anti-P7 oligonucleotides are then hybridized with the universal capture regions P5 and P7 of the capture primers, to produce double-stranded regions. In the next step, the target-specific capture regions of unhybridized capture primer are removed by exonuclease I, while the universal capture regions are protected in their double stranded configuration. After removal of the anti-P5 and anti-P7 oligonucleotides, the immobilized target polynucleotides can be further amplified by bridge amplification and sequenced.

In some embodiments, the application-specific capture region includes a target-specific capture region and the application-specific polynucleotide includes a target polynucleotide. In some embodiments, the methods further include extending the target-specific capture region of an application-specific capture primer hybridized to a target polynucleotide to produce an immobilized extension product complementary to the target polynucleotide. In some embodiments, the methods include annealing the universal capture primer to the immobilized extension product. In some embodiments, the methods include amplifying by PCR the immobilized extension product to produce a plurality of immobilized amplicons. In some embodiments, the methods include sequencing the plurality of immobilized amplicons. In some embodiments, sequencing comprises a bridge amplification step.

Figure 10:
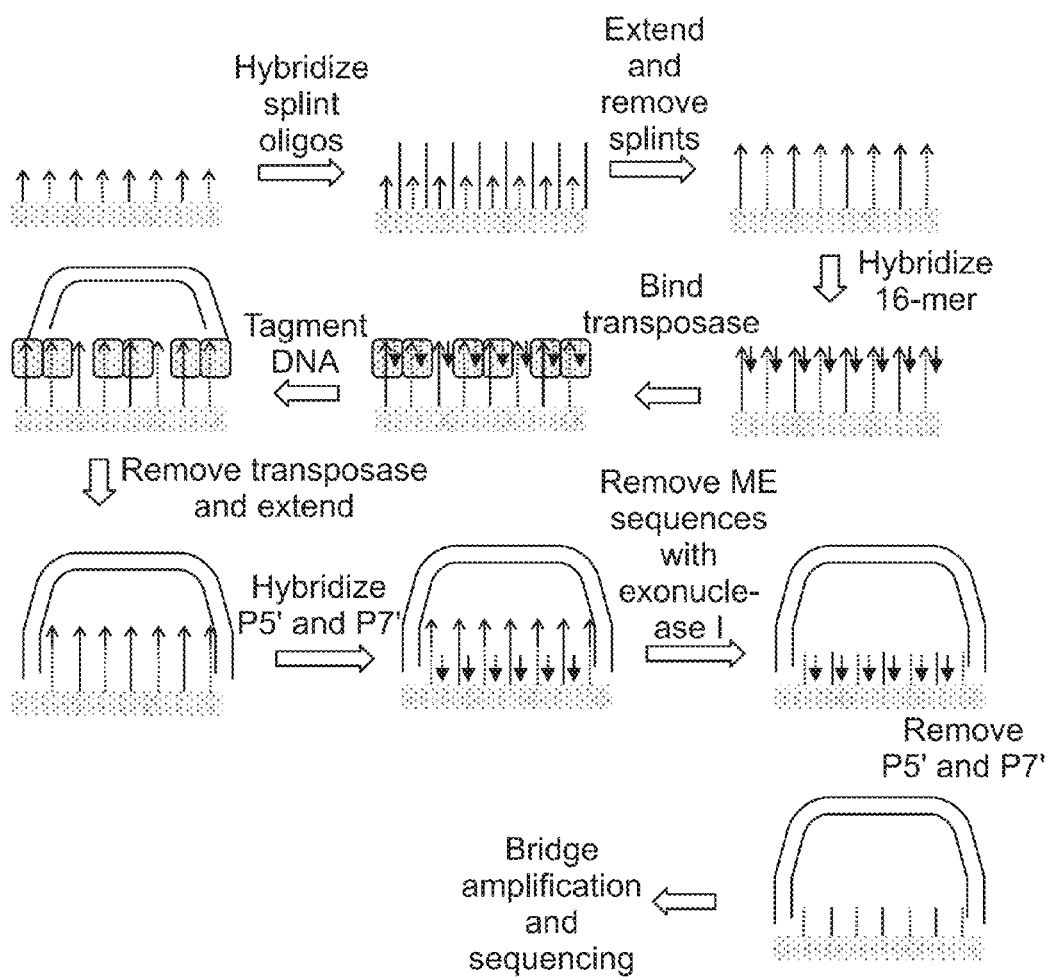
FIG. 10 is a schematic illustrating the removal of transposon end regions from application-specific capture primers in a surface tagmentation experiment.

In some embodiments, the methods of this disclosure are used in surface tagmentation applications. The general design of a tagmentation experiment is illustrated in FIG. 10. First, transposon end regions (e.g., ME) are added to the 3' ends of universal capture primers using the primer hybridization and extension method. Next, a transposon end oligonucleotide is hybridized to the transposon end regions to form a double-stranded transposon end. Transposase is bound to transposon ends, thereby producing surface transposomes. In some embodiments, transposase is bound to all double-stranded transposon ends. In other embodiments, transposase is bound to less than all double-stranded transposon ends (e.g., less than 99%, 95%, 90%, 80%, 70%, 60%, 50%, 40%, 30%, 20%, 10%, 5% or 1%). A target polynucleotide is tagmented directly onto the surface. Tagmented target polynucleotides include, e.g., genomic DNA. Tagmentation includes joining the 3'-strand of the extended universal primer with a target polynucleotide strand, thereby immobilizing the target polynucleotide. In some embodiments, transposase complexes and transposon end oligonucleotides are removed and a round of target polynucleotide extension follows (see, e.g., FIG. 10). The universal capture regions of the capture primers (e.g., P5 and P7 regions) are protected from exonuclease digestion by hybridization with complementary oligonucleotides (anti-P5 and anti-P7) to turn these regions into double-strands. Single-stranded transposon end regions are removed with exonuclease I. Bridge amplification is performed and resulting target polynucleotide clusters are prepared for sequencing.

In some embodiments, the application-specific capture region includes a transposon end (TE) region and the application-specific polynucleotide includes a TE oligonucleotide. In some embodiments, the methods further include binding a transposase to the TE-region—TE oligonucleotide (TEO) hybrid after execution of step b) and prior to execution of step c) to produce a support-bound transposome complex. In some embodiments, the methods further include contacting the support-bound transposome complex with a target polynucleotide under conditions wherein the support-bound transposome complex joins the 3'-end of the TE region in the application-specific capture primer (the "transferred strand") to the target polynucleotide to produce an immobilized target polynucleotide. In some embodiments, the methods further include extending the 3'-end of the immobilized target polynucleotide. In some embodiments, the methods further include removing the transposase and TEO from the solid support. In some embodiments, the methods further include extending the 3'-end of the immobilized target polynucleotide. In some embodiments, the methods further include amplifying by PCR the immobilized target polynucleotide to produce a plurality of immobilized amplicons. In some embodiments, the methods further include sequencing the plurality of immobilized amplicons. In some embodiments, sequencing includes bridge amplification.

In some embodiments, the methods of this disclosure improve the sequencing data quality or the sequencing data quantity in a direct target capture application or in a surface tagmentation application relative to a control wherein a method of this disclosure was not performed (see, e.g., Example II). In some embodiments, the methods lower the percent mismatch rate (%PF; purity filter). In certain embodiments, the % mismatch rate in a surface tagmentation application is less than 0.6%, 0.5%, 0.4%, 0.3%, 0.2%, or less. In some embodiments, the methods increase the percent of bases above Q30 (a probability of greater than 1 in 1,000 that the base is correct). In certain embodiments, the percent of bases above Q30 in a surface tagmentation application is greater than 90%, 91%, 92%, 93%, 94%, 95%, 96%, or more. In some embodiments, the methods increase the percent of PF clusters (%PF, the number of clusters crossing a minimum signal threshold). In certain embodiments, the methods increase the percent of PF clusters in a surface tagmentation application to greater than 70%, 75%, 80%, 85% or more. In some embodiments, the methods increase the percentage of aligned reads (% align (PF)). In certain embodiments, the method increases the percentage of aligned reads to greater than 70%, 75%, 80%, 85%, or 90%.

The present disclosure further relates to amplification of immobilized nucleic acid fragments produced according to the methods provided herein. Immobilized nucleic acid fragments can include, for example, immobilized extension products that are complementary to target polynucleotides captured as part of a direct capture application. In another example, immobilized nucleic acid fragments can include, target polynucleotides that are immobilized in the course of a tagmentation application. The immobilized nucleic acid fragments can be amplified according to any suitable amplification methodology known in the art. In some embodiments, the immobilized nucleic acid fragments are amplified on a solid support. In some embodiments, the solid support is the same solid support upon which the surface bound tagmentation occurs. In such embodiments, the methods and compositions provided herein allow sample preparation to proceed on the same solid support from the initial sample introduction step through amplification and optionally through a sequencing step.

For example, in some embodiments, the immobilized nucleic acid fragments are amplified using cluster amplification methodologies as exemplified by the disclosures of U.S. Pat. Nos. 7,985,565 and 7,115,400, the contents of each of which is incorporated herein by reference in its entirety. The incorporated materials of U.S. Pat. Nos. 7,985,565 and 7,115,400 describe methods of solid-phase nucleic acid amplification which allow amplification products to be immobilized on a solid support in order to form arrays included of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons. Other suitable methodologies can also be used to produce immobilized amplicons from immobilized nucleic acid fragments produced according to the methods provided herein. For example one or more clusters or colonies can be formed via solid-phase PCR whether one or both primers of each pair of amplification primers are immobilized.

In other embodiments, the immobilized nucleic acid fragments are amplified in solution. For example, in some embodiments, the immobilized nucleic acid fragments are cleaved or otherwise liberated from the solid support and amplification primers are then hybridized in solution to the liberated molecules. In other embodiments, amplification primers are hybridized to the immobilized nucleic acid fragments for one or more initial amplification steps, followed by subsequent amplification steps in solution. Thus, in some embodiments an immobilized nucleic acid template can be used to produce solution-phase amplicons.

It will be appreciated that any of the amplification methodologies described herein or generally known in the art can be utilized with universal or target-specific primers to amplify the immobilized nucleic acid fragments. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods can be employed to amplify one or more nucleic acids of interest. For example, PCR, including multiplex PCR, SDA, TMA, NASBA and the like can be utilized to amplify immobilized DNA fragments. In some embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., Nat. Genet. 19:225-232 (1998), which is incorporated herein by reference) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference) technologies. It will be appreciated that these amplification methodologies can be designed to amplify immobilized nucleic acid fragments. For example, in some embodiments, the amplification method can include ligation probe amplification or oligonucleotide ligation assay (OLA) reactions that contain primers directed specifically to the nucleic acid of interest. In some embodiments, the amplification method can include a primer extension-ligation reaction that contains primers directed specifically to the nucleic acid of interest. As a non-limiting example of primer extension and ligation primers that can be specifically designed to amplify a nucleic acid of interest, the amplification can include primers used for the GoldenGate assay (Illumina®, Inc., San Diego, Calif.) as exemplified by U.S. Pat. Nos. 7,582,420 and 7,611,869, each of which is incorporated herein by reference in its entirety.

Exemplary isothermal amplification methods that can be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyperbranched strand displacement amplification which is described in, for example Lage et al., Genome Research 13:294-307 (2003), each of which is incorporated herein by reference in its entirety. Isothermal amplification methods can be used with the strand-displacing Phi 29 polymerase or Bst DNA polymerase large fragment, 5'->3' exo⁻ for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety.

Another nucleic acid amplification method that is useful in the present disclosure is Tagged PCR which uses a plurality of two-domain primers having a constant 5' region followed by a random 3' region as described, for example, in Grothues et al. Nucleic Acids Res. 21(5):1321-2 (1993), incorporated herein by reference in its entirety. The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers can be removed and further replication can take place using primers complementary to the constant 5' region.

The present disclosure further relates to sequencing of the immobilized target polynucleotides produced according to the methods provided herein. The immobilized target polynucleotides produced, for example, by surface bound transposome mediated tagmentation or direct target capture can be sequenced according to any suitable sequencing methodology, such as direct sequencing, including sequencing by synthesis, sequencing by ligation, sequencing by hybridization, nanopore sequencing and the like. In some embodiments, the immobilized target polynucleotides are sequenced on a solid support. In some embodiments, the solid support for sequencing is the same solid support upon which the surface bound tagmentation occurs. In some embodiments, the solid support for sequencing is the same solid support upon which the amplification occurs.

One preferred sequencing methodology is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

Flow cells provide a convenient solid support for housing amplified DNA fragments produced by the methods of the present disclosure. One or more amplified DNA fragments in such a format can be subjected to an SBS or other detection technique that involves repeated delivery of reagents in cycles. For example, to initiate a first SBS cycle, one or more labeled nucleotides, DNA polymerase, etc., can be flowed into/through a flow cell that houses one or more amplified nucleic acid molecules. Those sites where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with amplicons produced by the methods of the present disclosure are described, for example, in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210, 891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US 2005/0191698 A1, U.S. Pat. Nos. 7,595,883, and 7,244,559.

Some embodiments can utilize methods involving the real-time monitoring of DNA polymerase activity. For example, nucleotide incorporations can be detected through fluorescence resonance energy transfer (FRET) interactions between a fluorophore-bearing polymerase and y-phosphate-labeled nucleotides, or with zeromode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008).

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1. Methods set forth herein for amplifying target nucleic acids using kinetic exclusion can be readily applied to substrates used for detecting protons. More specifically, methods set forth herein can be used to produce clonal pluralities of amplicons that are used to detect protons.

Another useful sequencing technique is nanopore sequencing (see, for example, Deamer et al. Trends Biotechnol. 18, 147-151 (2000); Deamer et al. Acc. Chem. Res. 35:817-825 (2002); Li et al. Nat. Mater. 2:611-615 (2003). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al. Clin. Chem. 53, 1996-2001 (2007); Healy, Nanomed. 2, 459-481 (2007); Cockroft et al. J. Am. Chem. Soc. 130, 818-820 (2008).

Exemplary methods for array-based expression and genotyping analysis that can be applied to detection according to the present disclosure are described in U.S. Pat. Nos.7,582, 420; 6,890,741; 6,913,884 or 6,355,431 or US Pat. Pub. Nos. 2005/0053980 A1; 2009/0186349 A1 or US 2005/0181440 A1.

A beneficial use of the methods set forth herein is that they provide for rapid and efficient detection of a plurality of nucleic acid fragments in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized nucleic acid fragments, the system including components such as pumps, valves, reservoirs, fluidic lines and the like. A flow cell can be configured and/or used in an integrated system for detection of target nucleic acids. Exemplary flow cells are described, for example, in US 2010/0111768 A1 and U.S. Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina®, Inc., San Diego, Calif.) and devices described in U.S. Ser. No. 13/273,666.

The present disclosure further relates to kits for modifying an immobilized capture primer. In some embodiments, the kits include a) an application-specific capture primer, including i) a 3' portion including an application-specific capture region, and ii) a 5' portion including a universal capture region, and b) a nuclease. In other embodiments, the kits include a) a first universal capture primer; b) a second universal capture primer; c) an oligonucleotide including a region complementary to a region in the first universal capture primer and a region complementary to a region in an application-specific polynucleotide; d) an oligonucleotide including a region complementary to a region in the second universal capture primer and a region complementary to a region in an application-specific polynucleotide; and e) a nuclease. In some embodiments, the nuclease is an exonuclease. In some embodiments, the nuclease is exonuclease I. In some embodiments, the nuclease is exonuclease III. In some embodiments, the nuclease is an endonuclease. In some embodiments, the nuclease is a restriction endonuclease.

In some embodiments, the kits further include a substrate for the immobilization of the application-specific capture primer or the universal capture primers. In some embodiments, the kits further include one or more oligonucleotides including a regions that is complementary to a universal capture primer or a universal capture region. In some embodiments, the kits further include one or more oligonucleotides including a region that is complementary to a target-capture region. In some embodiments, the kits further include instructions for using the components of the kit for the modification of an immobilized capture primer. In some embodiments, the kits further include one or more control analyte mixture, e.g., two or more control analytes for use in testing the kit.

The present invention provides further methods of occupying a patterned flow cell with PCR amplified target DNA sequences.

Figure 13:
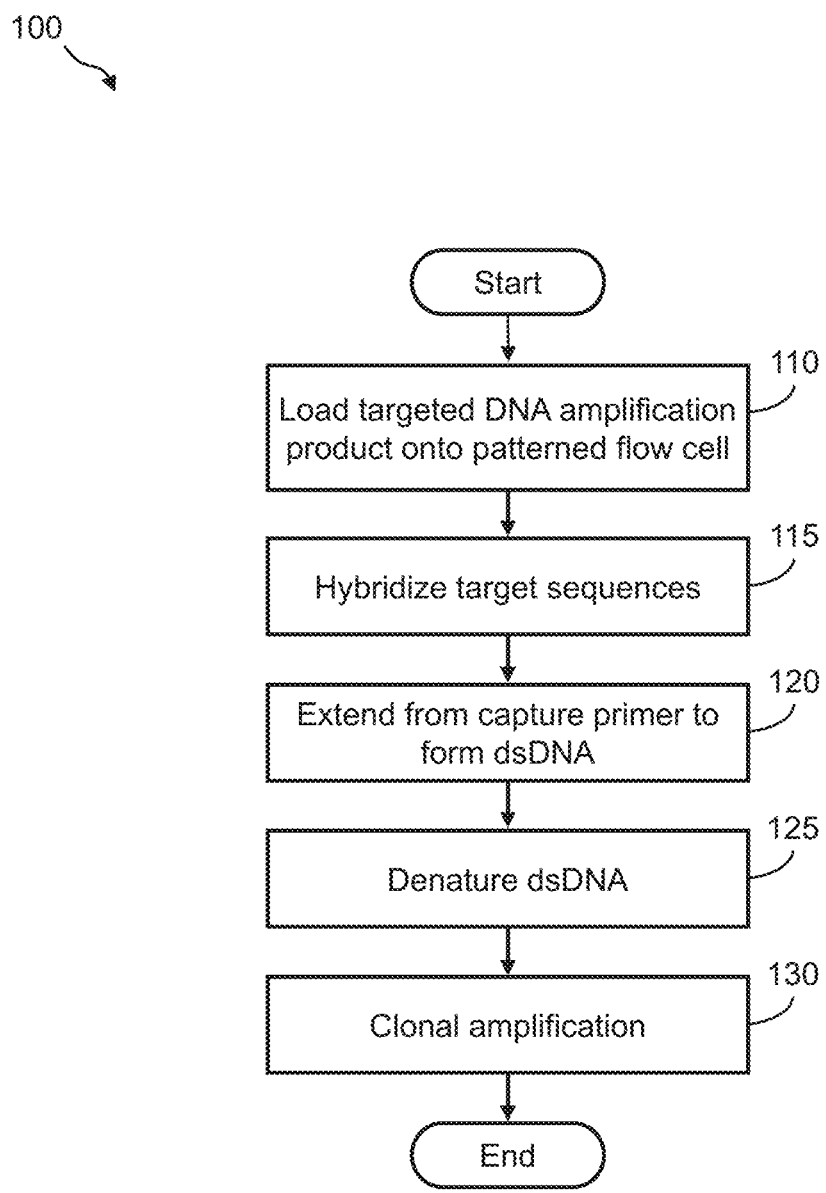
FIG. 13 illustrates a flow diagram of an example of a method of occupying a patterned flow cell with a targeted DNA amplification product.

FIG. 13 illustrates a flow diagram of an example of a method 100 of occupying a patterned flow cell with a targeted DNA amplification product. For example, targeted DNA amplification may be performed according to the methods described in the WO2010/038042 publication, the WO2011/025477 publication, the U.S. 61/928,368 patent application, and/or the U.S. 61/928,382 patent application. Method 100 uses a DNA polymerase mediated primer extension step and wash steps to separate seeding of amplified target DNA sequences on a flow cell surface from clonal amplification of captured target sequences. Method 100 includes, but is not limited to, the following steps.

At a step 110, a targeted DNA amplification product is loaded onto a patterned flow cell. The patterned flow cell includes gene-specific capture primers on the flow cell surface.

At a step 115, target sequences are hybridized to capture primers on the patterned flow cell. After an incubation period, the flow cell is washed to remove unbound sequences.

At a step 120, the capture primer is extended by DNA polymerase to create a complement of the hybridized target sequence. After an incubation period, the flow cell is washed.

At a step 125, the dsDNA is denatured. The flow cell is washed to remove the unbound original target sequence.

At a step 130, the bound single-stranded template is ready for clonal amplification and subsequent sequencing. In one example, the amplification method for occupying a patterned flow cell is a kinetic exclusion method. For example, kinetic exclusion may be performed according to the method described in the U.S. 20130338042 patent publication. In another example, the amplification method for occupying a patterned flow cell is bridge amplification (28 cycles).

Figure 14:
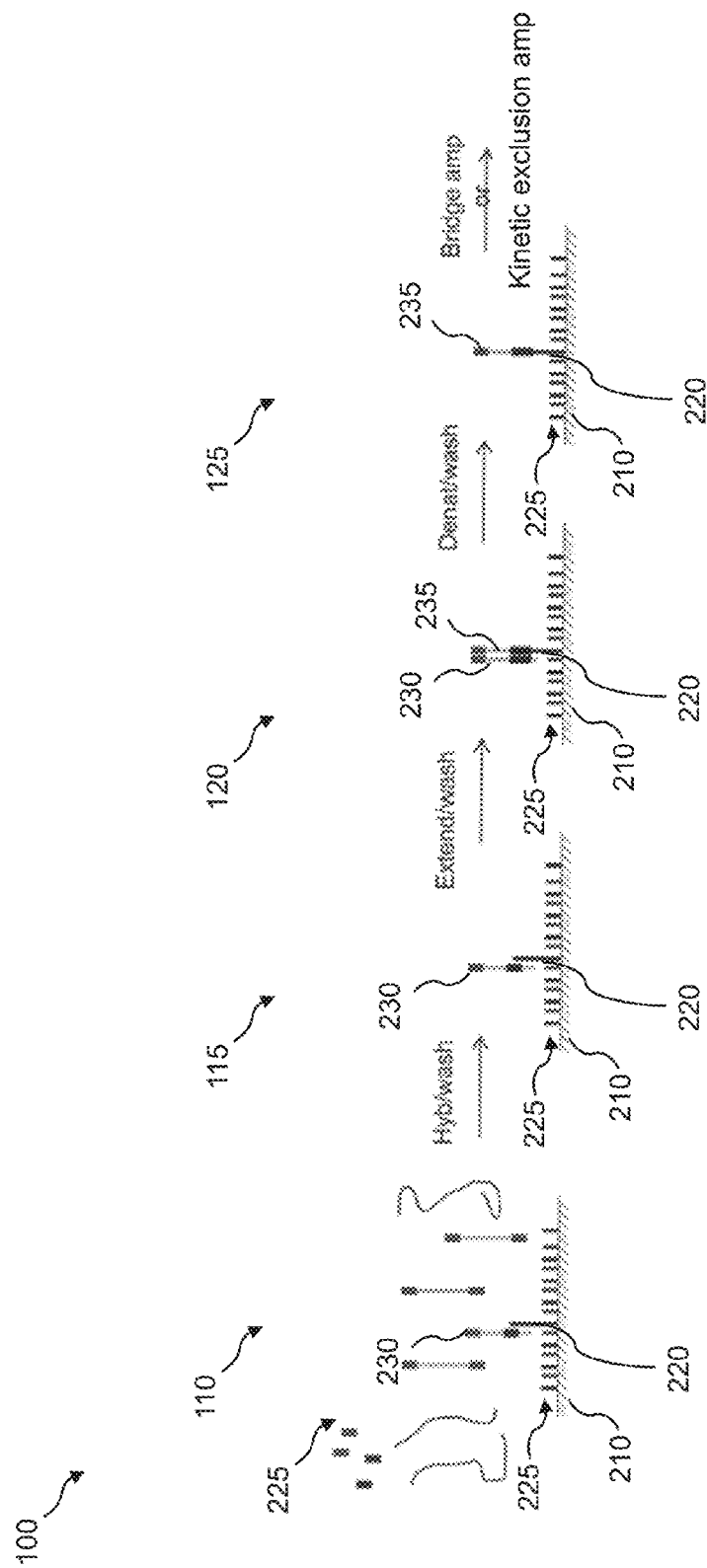
FIG. 14 shows pictorially the steps of the method of FIG. 13.

FIG. 14 shows pictorially the steps of method 100 of FIG. 13. Namely, a patterned flow cell 210 includes a capture primer 220 and a plurality of P5/P7 primers 225. Capture primer 220 includes oligonucleotide sequences specific for a target gene of interest. At step 110, targeted DNA amplification product 225 is loaded onto the surface of flow cell 210. Targeted DNA amplification product 225 includes target sequences 230 of interest, excess primers, and DNA. At step 115, target sequence 230 is hybridized to capture primer 220. At step 120, capture primer 220 is extended by DNA polymerase to create a complement 235 of the hybridized target sequence 230. At step 125, the dsDNA is denatured and the flow cell is washed to remove the unbound original target sequence 230.

Figure 15:
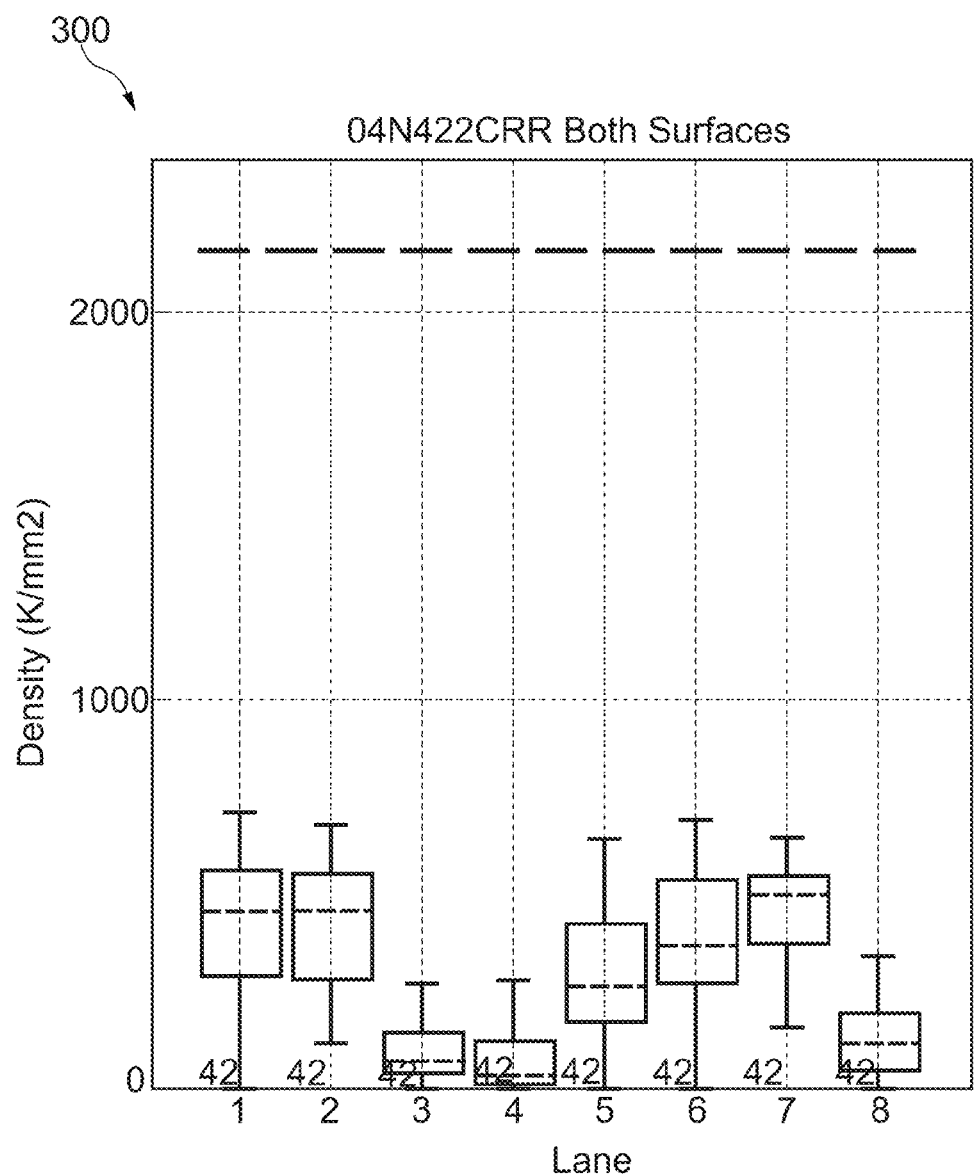
FIG. 15 shows a plot of cluster density by lane of a targeted DNA library prepared according to the method of FIG. 13.

FIG. 15 shows a plot 300 of cluster density by lane of a targeted DNA library prepared according to method 100 of FIG. 13. In this example, a patterned flow cell was prepared using different densities of capture probes: 25, 50, 100, or 200 pM. Template input was 10 μL or 2.5 μL of amplified target DNA. A summary of the probe density and template input is shown in Table A. The data show clusters that pass filter (green boxes) with an occupancy of about 30%. When clusters are analyzed, the least reliable data (often derived from overlapping clusters) is removed from the analysis results. Therefore, the raw data is filtered to remove any reads that do not meet the overall quality as measured by a chastity filter. The chastity of a base call is calculated as the ratio of the brightest intensity divided by the sum of the brightest and second brightest intensities. For example, clusters "pass filter (PF)" if no more than one base call in the first 25 cycles has a chastity of <0.6. The dashed bar represents the expected number of raw clusters/mm2. The data shows that with standard loading processes on a patterned flow cell, the percentage of clusters that pass filter is Poisson limited to about 30 to about 40%. This limitation is because the patterned array is seeded using a single template hybridization step, so Poisson loading predicts that some of the array will remain empty, some will have a single template, and others will have multiple templates.

TABLE A

Summary of probes and template by lane

| Lane | Probes | Template |
|---|---|---|
| 1 | 25 pM | 10 μL JAV + ve |
| 2 | 50 pM | 10 μL JAV + ve |
| 3 | 100 pM | 10 μL JAV + ve |
| 4 | 200 pM | 10 μL JAV + ve |
| 5 | 25 pM | 2.5 μL JAV + ve |
| 6 | 50 pM | 2.5 μL JAV + ve |
| 7 | 100 pM | 2.5 μL JAV + ve |
| 8 | 200 pM | 2.5 μL JAV + ve |

Figure 16:
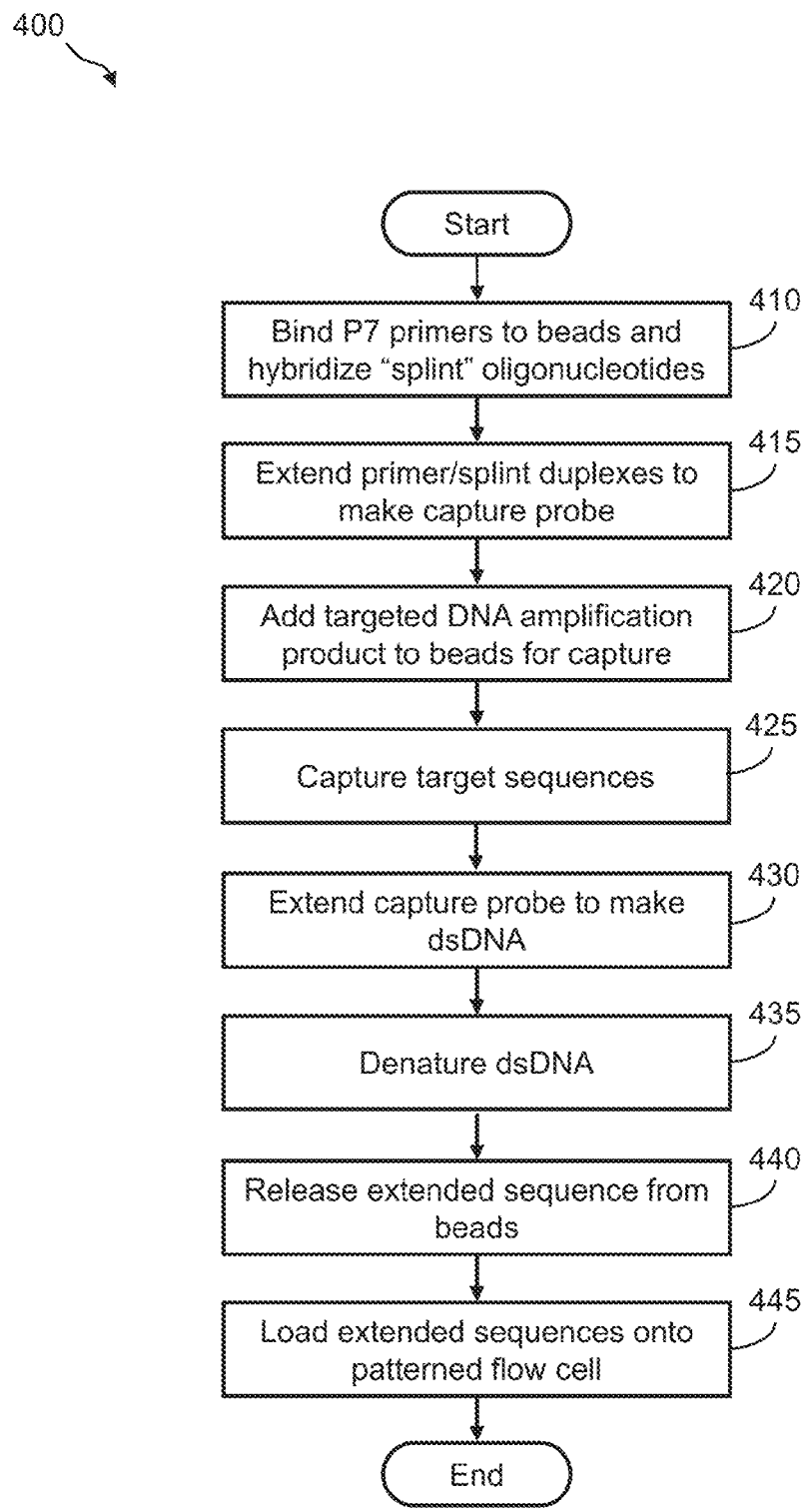
FIG. 16 illustrates a flow diagram of an example of a method of preparing a targeted DNA amplification product for a patterned flow cell.

FIG. 16 illustrates a flow diagram of an example of a method 400 of preparing a targeted DNA amplification product for a patterned flow cell. Method 400 uses bead-based target capture to pre-enrich target molecules prior to loading onto a patterned flow cell. Method 400 includes, but is not limited to, the following steps.

At a step 410, P7 primers are bound to a bead and a "splint" oligonucleotides are subsequently hybridized to the bound P7 primers. In one example, the P7 primers are biotinylated and the beads are streptavidin coated beads. The P7 primers are bound to the bead surface via a biotin-streptavidin binding complex. In another example, the P7 primers are bound to the bead using any suitable DNA chemistry that may be used to bind oligonucleotides to a solid surface. The "splint" oligonucleotide comprises a 3' sequence complimentary to the P7 primer (or part of it) and a 5' oligonucleotide sequence that includes a sequence complimentary to a capture probe sequence.

At a step 415, the bound P7/splint duplexes are extended to form the capture probe that is linked to the bead via its 5' end. The capture probe includes sequences that are specific for the target molecule of interest. A plurality of splints each containing a different complementary capture probe sequence may be linked to the bead.

At a step 420, a targeted DNA amplification product is added to a suspension of beads with the capture probe bound thereon.

At a step 425, target sequences in the targeted DNA amplification product are hybridized to the capture probes.

At a step 430, the capture probe is extended by DNA polymerase to create a compliment of the hybridized target sequence. The newly synthesized strand includes both P7 and P5 primers.

At a step 435, the dsDNA is denatured to remove the unbound original template. The newly synthesized complementary strand remains bound to the bead.

At a step 440, the complementary strand is released from the bead. In one example, the complementary strand bound to the bead by a biotin-streptavidin complex is released from the bead by boiling the bead suspension in water for a period of time sufficient to release the strands.

At a step 445, the P7-P5 primed targeted sequences are loaded onto a patterned flow cell for subsequent cluster generation and sequencing.

Figure 17:
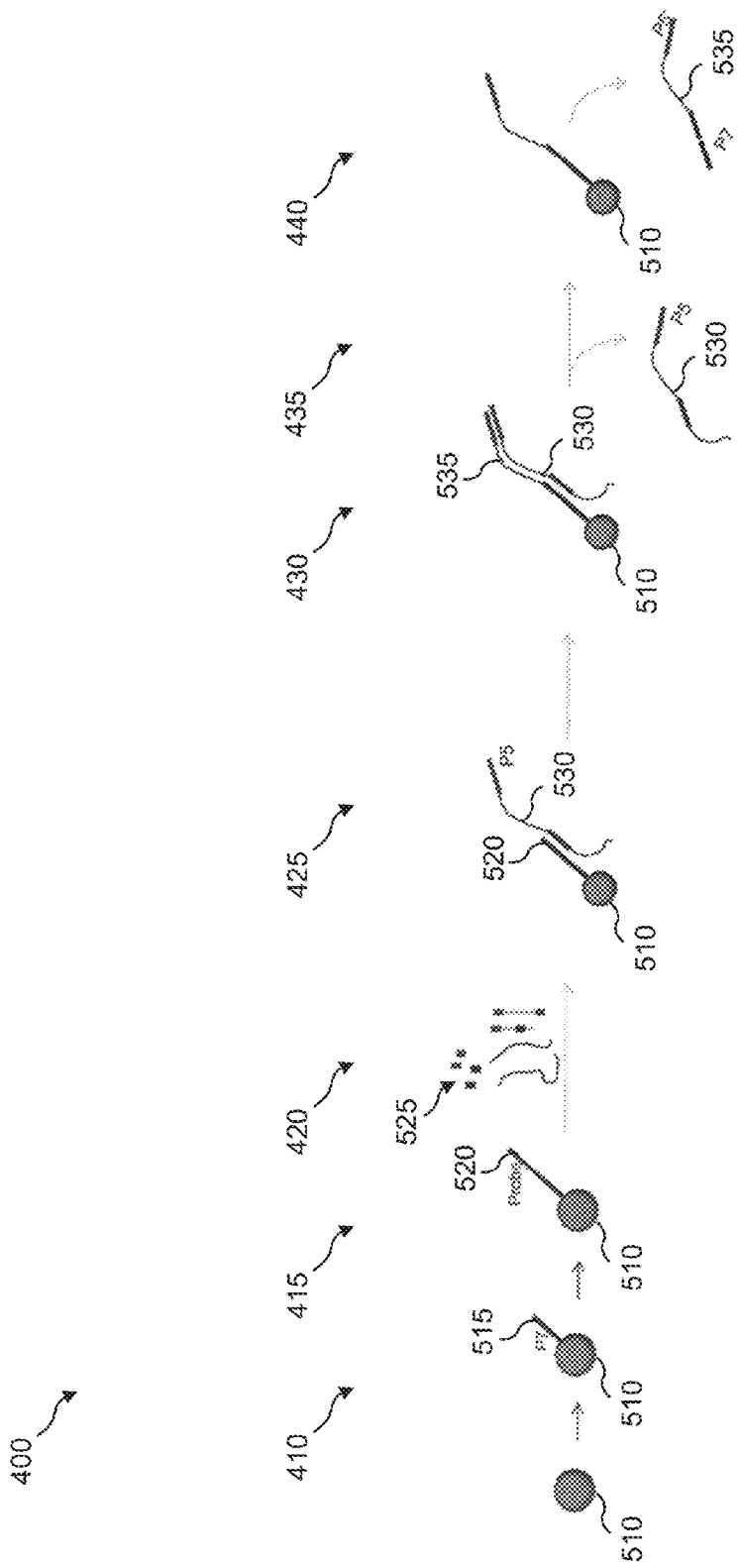
FIG. 17 shows pictorially the steps of the method of FIG. 16.

FIG. 17 shows pictorially the steps of method 400 of FIG. 16. Namely, a bead 510 is used to capture target sequences. At step 410, a P7 primer 515 is bound to bead 510 and a splint oligonucleotides (not shown) is hybridized to P7 primer 515. At step 415, the P7 primer/splint duplex is extended to form a capture probe 520. At step 420, a targeted DNA amplification product 525 is added to a suspension of beads 510 with the capture probe 520 bound thereon. At step 425, target sequences 530 contained in PCR product 525 are hybridized to capture probe 520. At step 430, capture probe 520 is extended by DNA polymerase to create a complementary strand 535 of target sequence 530. At step 435, the dsDNA is denatured to remove target sequence 530. At step 440, the extended complementary strand 535 is released from bead 510.

Figures 18A, 18B:
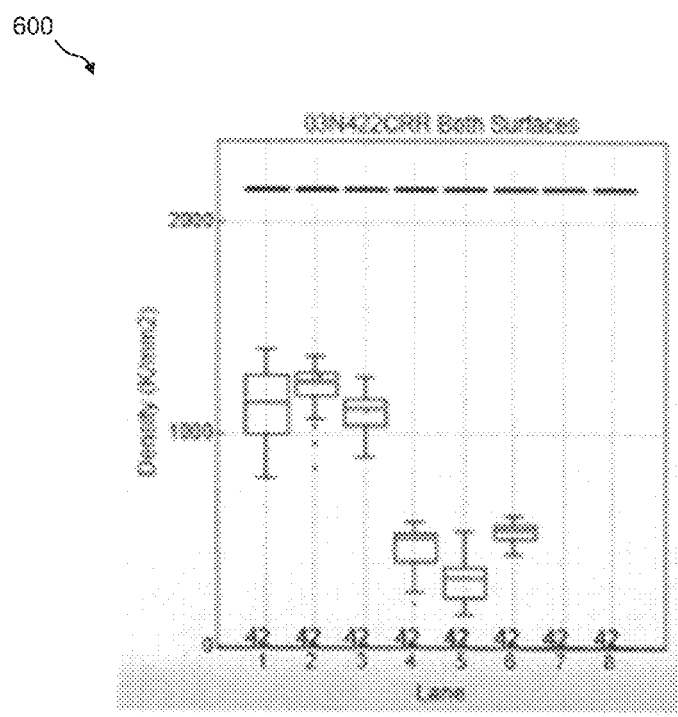
FIG. 18A and FIG. 18B show a plot of cluster density by lane and a summary data table of the sequence metrics for a bead-enriched targeted DNA library prepared according to the method of FIG. 16.

FIGS. 18A and 18B show a plot 600 of cluster density by lane and a summary data table 650 of the sequence metrics for a bead-enriched targeted DNA library prepared according to method 400 of FIG. 16. In this example, cluster generation and sequencing were performed on a pazam patterned flow cell. A control sample (CT13776) and extended (EXT) complementary ssDNA released from the beads were mixed with kinetic exclusion amplification reagents and loaded onto individual lanes of the flow cell as shown in data table 650. The control sample (CT13776) is a TruSeq PCR-free library derived from human genomic DNA. The EXT DNA are CPT-bead selected targeted DNA amplification products from an initial amplification using 10 ng of a Coriell human DNA sample. Referring to FIG. 18A, plot 600 shows the clusters passing filter for each lane of the patterned flow cell. The dashed line at the top of plot 600 is the expected raw density of features for a 700 nm pitch patterned flowcell. The boxes shown in plot 600 plot the actual number of clusters passing filter (per mm2). Referring to FIG. 18B, for lanes 2 and 3, the percent of clusters that pass filter (% PF Clusters) is about 50% to about 60% and show alignment (% Align (PF)) to the human genome of about 77%. The data show that CPT bead-enriched material may be used to efficiently load a patterned flow cell with PCR amplified target DNA sequences.

In some embodiments, low yield for the bead-based targeted capture can be overcome by substituting iminobiotin or desthiobiotin for biotin on the biotinylated P7 oligonucleotide. Low yield in certain situations can be attributed to the difficulty of eluting biotin from streptavidin. However, the use of iminobiotin creates a library product that can be efficiently bound to streptavidin at pH 7.5 or above and gently eluted at pH 4.0, room temperature with nearly 100% yield. Alternatively, substituting desthiobiotin for biotin creates a library product that can be efficiently bound to streptavidin and eluted with free biotin.

In certain targeted capture assay formats described herein, a biotin-P7 oligonucleotide is bound to streptavidin beads. After annealing of capture probes to the streptavidin bound P7 oligonucleotide, the capture probe sequences are attached to the bound P7 oligonucleotide by primer extension. Target asymmetric PCR products are annealed to the capture probes and serve as templates for strand extension. In certain embodiments, after washing, the single stranded biotinylated P7-capture probe-target DNA is eluted from the streptavidin beads by incubating in water at 100° C. for 5 minutes. This elution method can result in only a small fraction of ssDNA product being eluted from streptavidin by this process, leading to low library yield available for clustering. Substitution of iminobiotin for biotin leads to a library product that can be readily eluted from streptavidin with a pH shift to pH 4. Alternatively, substitution of desthiobiotin for biotin leads to a library product that can be readily eluted from streptavidin with free biotin. Both of these elution processes are gentle and can lead to nearly 100% library product recovery which may reduce the amount of DNA input required for library preparation leading to increased sensitivity. Any suitable form of iminobiotin can be used in the methods presented herein. Iminobiotin is not stable to certain conditions typically used for oligonucleotide deprotection after synthesis. An alternative method to incorporate iminobiotin is to couple NHS-iminobiotin to oligocapture probes modified with C6- or C12-modified amino groups. The desthiobiotin-TEG phosphoramidite is commercially available. The structure is shown below. Desthiobiotin can be incorporated into an oligonucleotide during regular synthesis.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The following examples are provided by way of illustration, not limitation.

EXAMPLE I

Removal of Transposon End Sequences from Capture Primers by Exonuclease

This example describes an integrated procedure for the conversion of universal capture primers to application-specific capture primers through primer hybridization and extension and the subsequent removal of application-specific capture regions by exonuclease.

Specifically, this example describes an experiment confirming the embodiment illustrated in FIG. 2B (modification of universal primers by primer hybridization and extension) and FIG. 3 (removal of application-specific region of modified primers by exonuclease I).

An experiment on an 8 lane flowcell was carried out using a list of conditions and controls as shown in Table 1 and FIGS. 9A-D.

Figure 9:
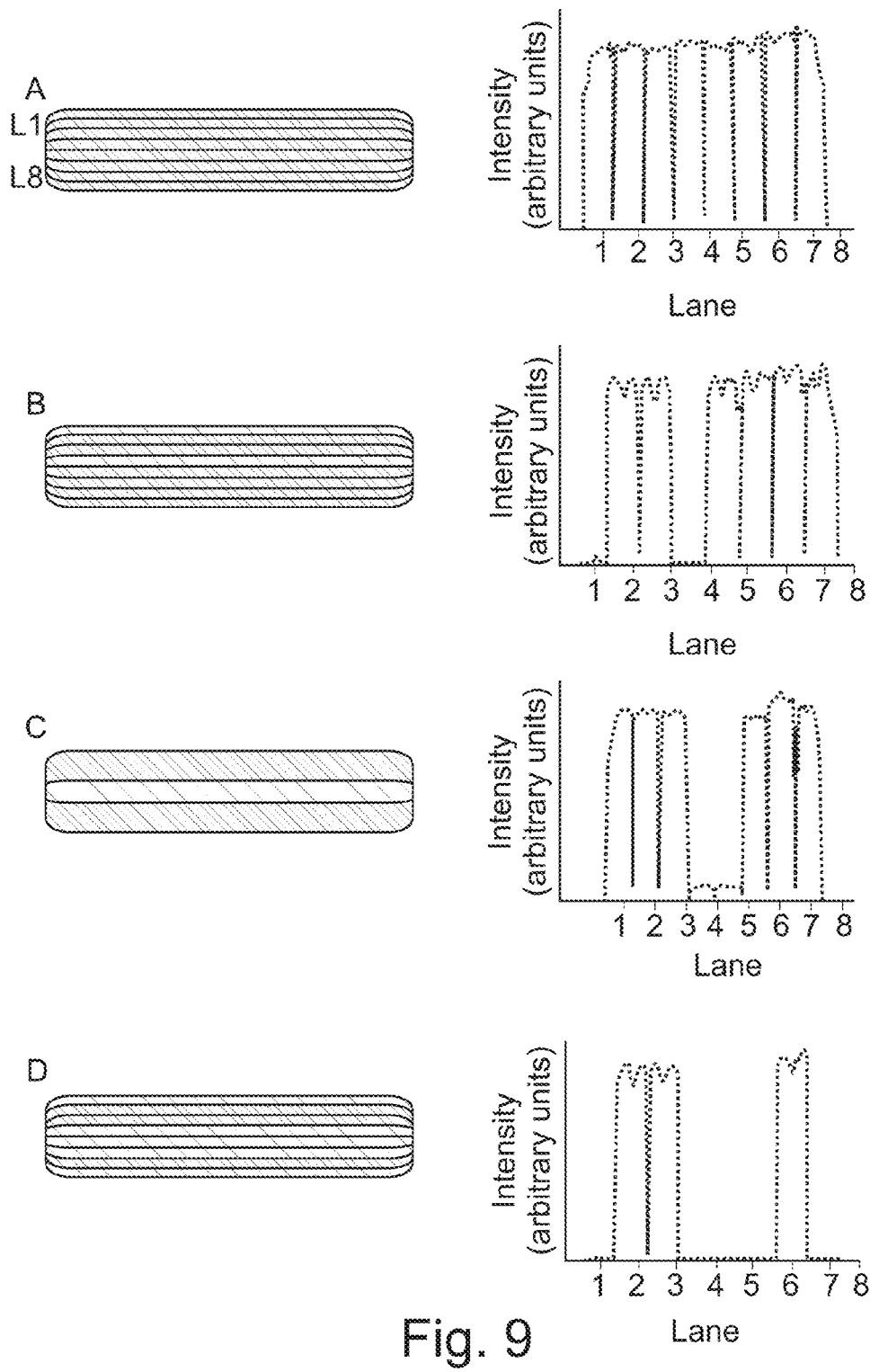
FIG. 9 shows the results of an experiment demonstrating the effective removal of application-specific capture regions from application-specific capture primers using exonuclease I. Application-specific capture primers having transposon end regions (ME regions) and universal capture regions (P5 and P7 regions) were immobilized on a flowcell, hybridized with labeled oligonucleotides and imaged on a Typhoon scanner. Flowcell images are shown on the left (L1, 2, 3, etc. indicate lanes 1, 2, 3 etc.). Plots showing quantified signals for each flowcell lane are shown on the right.

Transposon end regions (ME regions) were added to the 3' end of surface-bound P5 and P7 primers by hybridizing a splint oligonucleotide and copying it with a polymerase. ME sequences were added to flowcell lanes 2, 3, 5, 6, 7, and 8, but not to lanes 1 and 4. After removal of the splint oligonucleotides, the amount of surface-bound P5 and P7 sequences in each lane was assessed by using a primer density assay with labeled oligonuclotides (reverse complements of P5 ("anti-P5") and P7 ("anti-P7")). The result of this experiment is shown in FIG. 9A. All 8 lanes were shown to have a similar amount of surface-bound P5 and P7 sequences on the surface.

The relative amount of ME regions was assessed for each lane of the flow cell with a primer density assay using a labeled anti-ME oligonucleotide. The result of this experiment is shown in FIG. 9B. Lanes which were not subjected to the primer hybridization and extension protocol (lanes 1 and 4) showed no ME-specific signal. By contrast, lanes which were subjected to primer hybridization and extension (lanes 2, 3, 5, 6, 7, and 8) showed strong ME-specific signals.

To protect the universal capture regions (P5 and P7 regions) of target-specific capture primers from exonuclease I digestion, anti-P5 and P7 oligonucleotides were hybridized to lanes 3, 6, 7 and 8. Lanes 4, 5, 6 and 8 were then treated with exonuclease I for 30 minutes at 38° C. The experimental design is summarized in Table 1.

TABLE 1

Design of Exonuclease Digest Experiment

| Lane | Splint Oligo | Anti-P5 & Anti-P7 | Exonuclease | Signal (labeled Anti-P5 & Anti-P7) | Signal (labeled anti-ME) |
|---|---|---|---|---|---|
| 1 | No | No | No | + | − |
| 2 | Yes | No | No | + | + |
| 3 | Yes | Yes | No | + | + |
| 4 | No | No | Yes | − | − |
| 5 | Yes | No | Yes | − | − |
| 6 | Yes | Yes | Yes | + | − |
| 7 | Yes | Yes | No | + | + |
| 8 | Yes | Yes | Yes | + | − |

The last two columns of Table 1 represent the observed P5/P7- and ME-specific signals in each flowcell lane. A plus indicates that a strong signal was observed, whereas a minus indicates that only a weak or background signal was observed. The results of this experiment are also shown in FIGS. 9C and 9D.

The anti-P5 and anti-P7 oligonucleotides were found to effectively protect the universal P5 and P7 regions of the capture primers. For example, strong signals were observed in lanes 6 and 8, where the P5 and P7 regions were protected by hybridization with anti-P5 and anti-P7 oligonucleotides. By contrast, P5 or P7-specific signal was not observed in lane 4, where the P5 and P7 regions of capture primers remained unhybridized and single-stranded.

These results show exonuclease can effectively remove unhybridized, single-stranded capture primers, but that single-stranded primers can be protected from exonuclease by hybridization with complementary oligonucleotides.

Exonuclease was shown to effectively remove target-specific ME regions from capture primers. Lane 6, where the universal capture regions of the capture primers were protected from exonuclease, showed no ME-specific signal. By contrast, lane 7, which was not subjected to exonuclease treatment showed a strong signal.

In summary, the results shown in this Example demonstrate that primer extension and hybridization is an effective method for adding target-specific capture regions (e.g., ME regions) to the 3' ends of immobilized universal capture primers, thereby producing target-specific capture primers. Exonuclease can be used to remove unhybridized target-specific capture regions and thereby convert target-specific capture primers to universal capture primers. The universal capture regions of universal capture primers (e.g., P5 and P7 regions) can be protected from exonuclease by hybridization with complementary oligonucleotides (e.g., anti-P5 and anti-P7 oligonucleotides).

EXAMPLE II

Removal of Transposon End Regions from Capture Primers Promotes Bridge Amplification Following Surface Tagmentation This example describes an integrated procedure for DNA immobilization through surface tagmentation, removal of unhybridized transposon end regions, bridge amplification and sequencing of amplicons.

Figure 7:
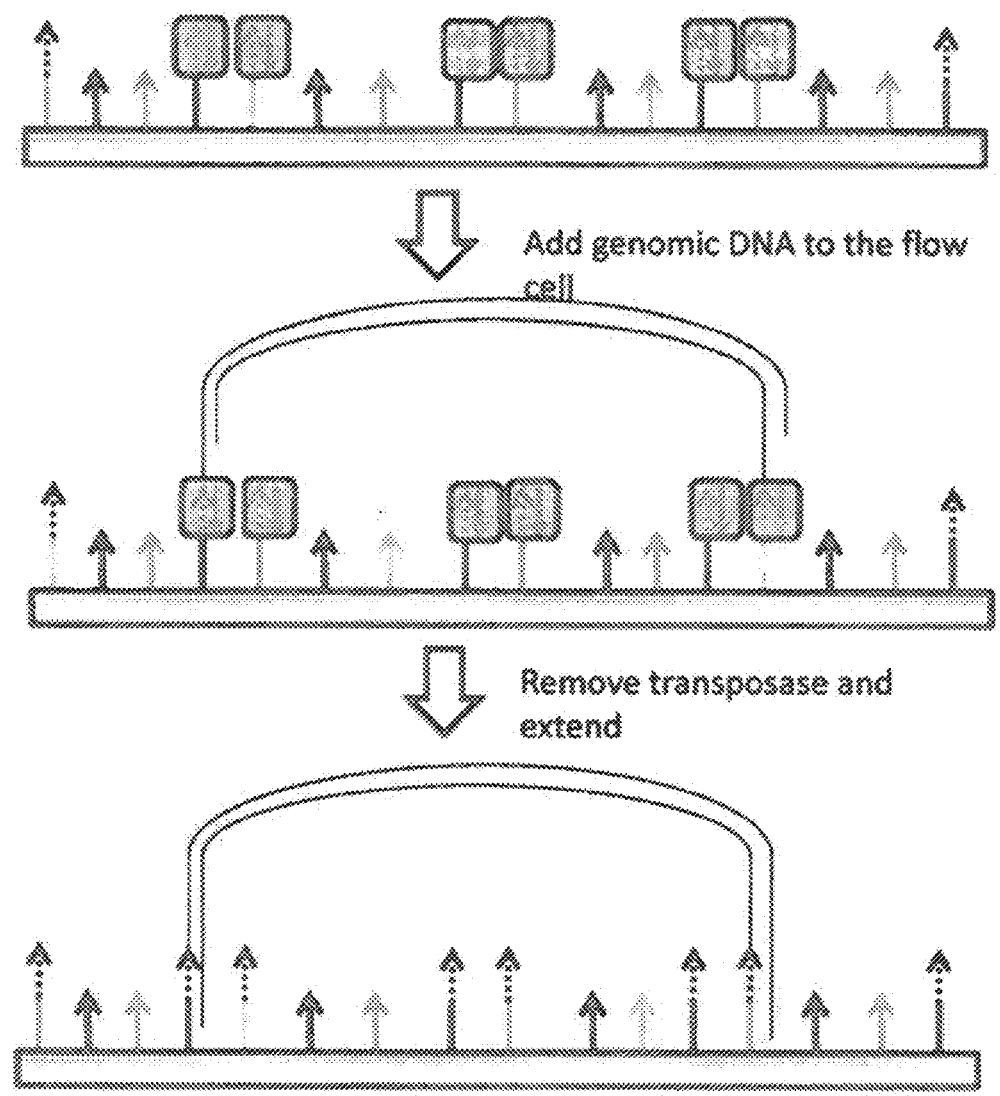
FIG. 7 is a schematic illustrating a surface tagmentation reaction.

Specifically, this example describes an experiment confirming the embodiment illustrated in FIG. 6 (preparation of a flow cell for surface tagmentation), FIG. 7 (surface tagmentation reaction), and FIG. 10 (surface tagmentation followed by removal of transposon end regions).

Flowcells can be prepared for surface tagmentation, e.g., according to the protocol illustrated in FIG. 6. First, splint oligonucleotides, which contain a region complementary to universal capture primers (e.g., P5 or P7) and a region complementary to a transposon end region (e.g., the mosaic end (ME)), are hybridized to universal capture primers on a standard Illumina® flow cell. Next, the universal capture primers are extended at their 3'-ends to add a transposon end region. After removal of the splint oligonucleotides, a transposon end oligonucleotide is hybridized to the transposon end region of the extended capture primers to form transposon ends. Transposase is then bound to the transposon ends. Transposon end regions which are not bound to a transposase and are not part of a viable transposome can impede bridge amplification, as shown below.

Surface tagmentation can be performed, e.g., according to the protocol illustrated in FIG. 7. First, genomic DNA (the exemplary target polynucleotide) is flowed inside a flowcell with surface-bound transposomes. These transposomes can fragment and immobilize the genomic DNA in a "tagmentation reaction". In the course of this reaction, the 3'-end of an extended primer (the "transferred strand") is joined to the target DNA, which is thereby immobilized to the flow cell (the immobilized target polynucleotide). After completion of the tagmentation reaction the transposase molecules are removed (for example with PBI (Quiagen buffer)) and the 3' ends in the target DNA, which were generated during the tagmentation reaction, are extended. After the removal of transposomes an excess of extended capture primers with transposon regions remain.

The presence of excess target-specific capture primers has generally been found to lower the data quality and data quantity of sequencing reactions relative to similar reactions conducted on unmodified standard flow cells which contain only universal capture primers. For example, % PF values were found to be lower, the percentile of bases above Q30 was found to be lower, and the background signals observed when imaging clusters in the initial SBS (sequencing by synthesis) cycles were found to be higher when using modified Illumina® flowcells having excess target-specific capture primers than when using unmodified standard Illumina® flowcells having only universal capture primers.

Figure 8:
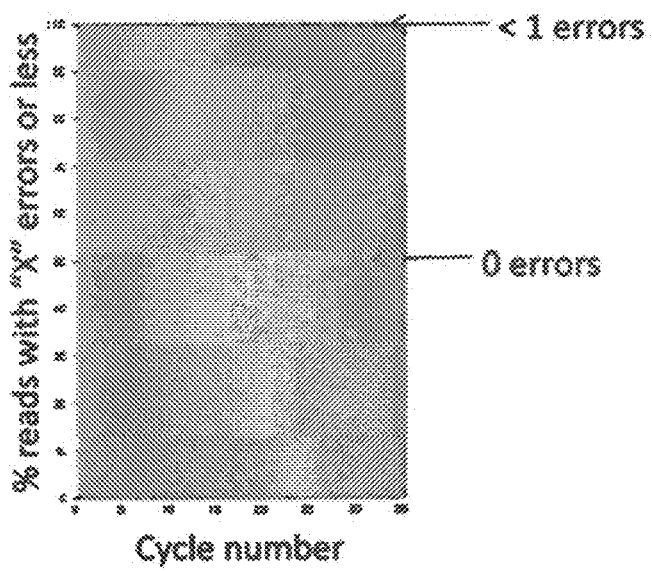
FIG. 8 shows a comparison of DNA sequencing results obtained on an unmodified Illumina® flowcell having only universal capture primers, also referred to as standard Illumina® surface primers (Lane 1, top panel) and on a modified Illumina® flowcell having application-specific capture primers, also referred to as modified surface primers P5-ME and P7-ME (Lane 2, bottom panel).
Figure 8:
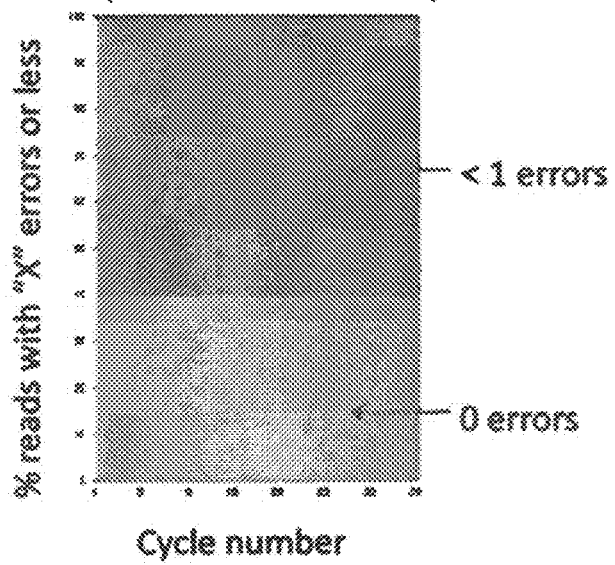

In one specific example, the effect of target-specific capture primers was demonstrated by sequencing a standard NEXTERA™ library on an unmodified standard Illumina® surface (having standard P5 and P7 primers) and on a surface having capture primers including transposon end regions (P5-ME and P7-ME primers). The results of this experiment are shown in Table 2 and FIG. 8.

TABLE 2

Experimental results for the sequencing of a NEXTERA™ library.

| | Clusters (raw) | % PF Clusters | % Mismatch Rate | % ≥Q30 bases (PF) |
|---|---|---|---|---|
| Lane 1 | 4,111,182 | 95.58 | 0.12 | 99.09 |
| Lane 2 | 3,049,165 | 88.97 | 1.70 | 96.12 |

Table 2 shows that the standard Illumina® surface (lane 1) yielded more data (higher raw cluster count) and also higher % PF and the data obtained was of higher quality (lower error rate with more bases above Q30) as compared to the modified surface (lane 2).

FIG. 8B shows the fraction of perfect reads (light gray area) and the fraction of reads containing one error (dark gray area). While the vast majority of reads obtained from the standard Illumina® surface (lane 1) were error free, approximately 60% of reads obtained from the modified surface (lane 2) had at least one error.

The following tagmentation experiment illustrates that the quality of DNA sequencing data can be improved by removing transposon regions from extended capture primers after completion of the tagmentation reaction and prior to bridge amplification.

Figure 11:
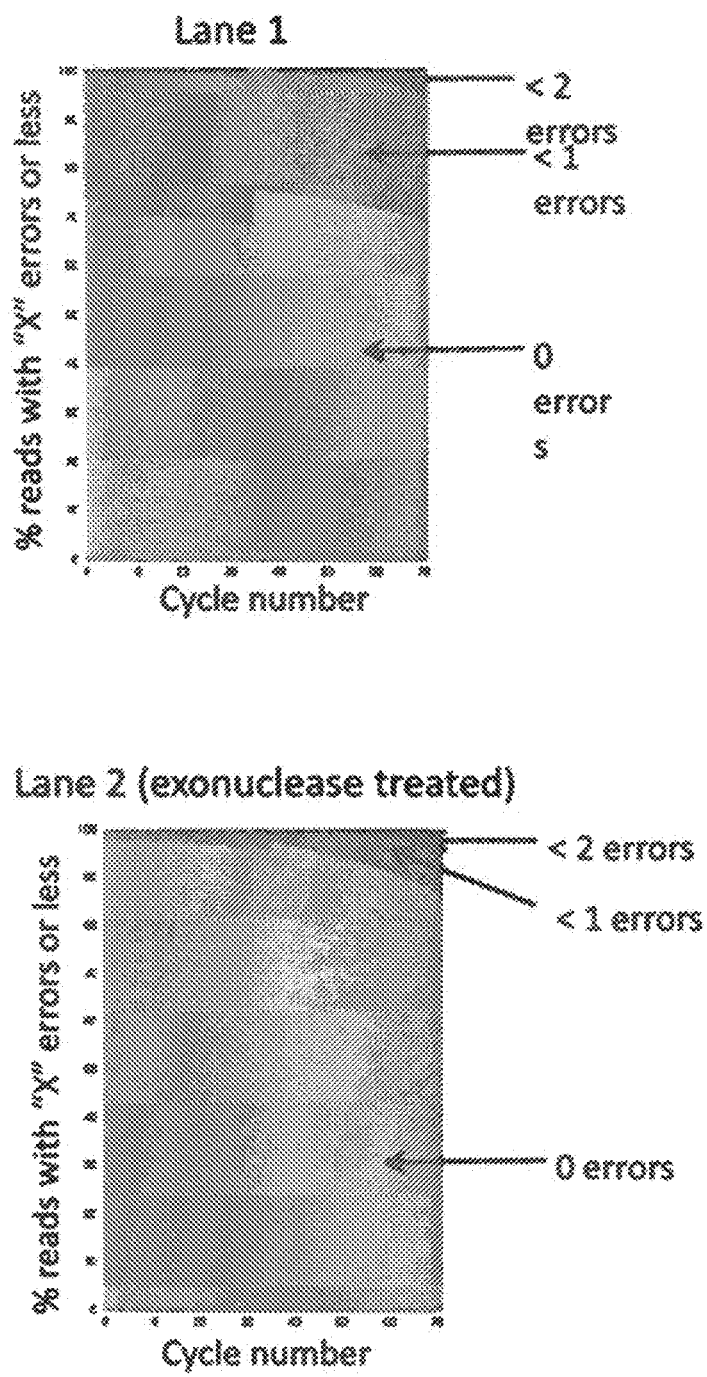
FIG. 11 shows the results of a surface tagmentation experiment comparing the proportions of perfect amplification clusters observed without removal of transposon end regions (Lane 1, top panel) or after removal of transposon end regions (ME regions) by exonuclease I (Lane 2, bottom panel).

An experiment on an 8 lane flow cell was carried out using a list of conditions and controls as shown in FIG. 11 and Tables 3 and 4.

TABLE 3

Experimental conditions of a tagmentation experiment.

| Lane | Surface Transposomes | P5 and P7 Rev Comp | Exonuclease Treatment | DNA |
|---|---|---|---|---|
| 1 | Yes | Yes | No | 200 ng E. coli genomic DNA |
| 2 | Yes | Yes | Yes | 200 ng E. coli genomic DNA |
| 3 | Yes | Yes | No | 200 ng E. coli genomic DNA |
| 4 | Yes | Yes | Yes | 200 ng E. coli genomic DNA |
| 5 | No | No | No | Standard phi X library |
| 6 | Yes | Yes | Yes | 200 ng E. coli genomic DNA |
| 7 | Yes | Yes | No | 200 ng E. coli genomic DNA |
| 8 | Yes | Yes | Yes | 200 ng E. coli genomic DNA |

* Experiment No.: 130618_EAS89_0423_FC664KHAAX

TABLE 4

Experimental results of a tagmentation experiment.

| Lane | % PF Clusters | % Align (PF) | % Mismatch Rate (PF) | % ≥Q30 bases (PF) |
|---|---|---|---|---|
| 1 (200 ng) | 68.2 | 71.54 | 0.85 | 89.34 |
| 2 (200 ng) | 82.83 | 73.7 | 0.16 | 95.5 |
| 3 (200 ng) | 67.64 | 69.27 | 0.79 | 88.7 |
| 4 (200 ng) | 82.79 | 75.96 | 0.15 | 95.5 |
| 5 phi X | 94.25 | 99.03 | 0.09 | 99.34 |
| 6 (500 ng) | 83.33 | 83.52 | 0.15 | 95.56 |
| 7 (500 ng) | 71.69 | 81.8 | 0.66 | 89.15 |
| 8 (500 ng) | 83.85 | 88.61 | 0.17 | 95.93 |

Table 4 shows the main sequencing metrics from the tagmentation experiment.

In lanes 2, 4, 6, and 8, the transposon end sequences of the target-specific capture primers were removed with exonuclease I prior to bridge amplification. The sequencing data in these lanes showed improved quality in terms of higher % PF and higher % align and a lower error rate relative to the data of lanes 1, 3 and 7, which remained untreated by exonuclease.

FIG. 11 shows the proportions of perfect clusters (light gray area) and clusters with 1 or 2 errors (dark gray and black areas respectively). Lane 2 in which the transposon end sequences were removed with exonuclease I prior to cluster amplification showed a larger proportion of perfect clusters (light gray area) compared to lane 1, which remained untreated by exonuclease.

In summary, this example demonstrates that removal of unhybridized application-specific capture regions from application-specific capture primers after immobilization of application-specific polynucleotides, but prior to bridge amplification substantially improves the DNA sequence data quality and quantity.

Although the disclosure has been described with reference to the disclosed embodiments, those skilled in the art will readily appreciate that the specific examples and studies detailed above are only illustrative of the disclosure. It should be understood that various modifications can be made without departing from the spirit of the disclosure. Accordingly, the disclosure is limited only by the following claims.

What is claimed:

1. A method of modifying an immobilized capture primer comprising:
   a. providing a solid support having an immobilized application-specific capture primer, the application-specific capture primer comprising:
      i. a 3' portion comprising an application-specific capture region, and
      ii. a 5' portion comprising a universal capture region;
   b. contacting an application-specific polynucleotide with the application-specific capture primer under conditions sufficient for hybridization to produce an immobilized application-specific polynucleotide, and
   c. removing the application-specific capture region of an application-specific capture primer not hybridized to an application-specific polynucleotide to convert the unhybridized application-specific capture primer to a universal capture primer.

2. The method of claim 1, wherein the application-specific capture primer comprises a plurality of different immobilized application-specific capture primers.

3. The method of claim 1, wherein the application-specific polynucleotide comprises a plurality of different application-specific polynucleotides.

4. The method of claim 1, wherein a portion of the application-specific capture region is removed.

5. The method of claim 1, wherein the application-specific capture region comprises a target-specific capture region and wherein the application-specific polynucleotide comprises a target polynucleotide.

6. The method of claim 5, further comprising extending the target-specific capture region of an application-specific capture primer hybridized to a target polynucleotide to produce an immobilized extension product complementary to the target polynucleotide.

7. The method of claim 6, further comprising annealing the universal capture primer to the immobilized extension product.

8. The method of claim 7, further comprising amplifying by PCR the immobilized extension product to produce a plurality of immobilized amplicons.

9. The method of claim 8, further comprising sequencing the plurality of immobilized amplicons.

10. The method of claim 1, wherein the application-specific capture region comprises a transposon end (TE) region and wherein the application-specific polynucleotide comprises a TE oligonucleotide.

11. The method of claim 10, further comprising binding a transposase to the TE region—TE oligonucleotide hybrid after execution of step b) and prior to execution of step c) to produce a support bound transposome complex.

12. The method of claim 11, further comprising contacting the support bound transposome complex with a target polynucleotide under conditions wherein the support-bound transposome complex joins the 3'-end of the TE region in the application-specific capture primer (the "transferred strand") to the target polynucleotide to produce an immobilized target polynucleotide.

13. The method of claim 1, wherein the universal capture region comprises a known sequence.

14. The method of claim 1, further comprising applying an oligonucleotide before execution of step c) under conditions sufficient for the oligonucleotide to hybridize with the universal capture region of an application-specific capture primer to produce a double-stranded DNA region.

15. The method of claim 1, further comprising contacting the application-specific capture primer with a nuclease, wherein the application-specific capture region of an application-specific capture primer not hybridized with an application-specific polynucleotide is removed by the nuclease.

16. The method of claim 15, wherein the nuclease is an exonuclease.

17. A method of modifying an immobilized capture primer comprising:
   a. providing a solid support having an immobilized application-specific capture primer, said application-specific capture primer comprising:
      i. a 3' portion comprising a target-specific capture region, and
      ii. a 5' portion comprising a universal capture region;
   b. contacting a target polynucleotide with the application-specific capture primer under conditions sufficient for hybridization to produce an immobilized target-specific polynucleotide;
   c. extending the application-specific capture primer hybridized to the immobilized target-specific polynucleotide to produce an immobilized extension product complementary to the immobilized target-specific polynucleotide;
   d. applying an oligonucleotide under conditions sufficient for the oligonucleotide to hybridize with the universal capture region of the immobilized application-specific capture primer;
   e. contacting the immobilized application-specific capture primer with nuclease under conditions sufficient for the nuclease to remove the target-specific capture region of an application-specific capture primer not hybridized to the immobilized target-specific polynucleotide to convert the unhybridized application-specific capture primer to a universal capture primer;

f. removing the oligonucleotide from the universal capture primer;

g. annealing the universal capture primer to the immobilized extension product;

h. amplifying the immobilized extension product to produce a plurality of immobilized amplicons, wherein amplifying comprises a bridge amplification step, and i. sequencing the plurality of immobilized amplicons.

18. The method of claim 17, wherein the nuclease is an exonuclease.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
aatgatacgg cgaccaccga                                              20

```
<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
caagcagaag acggcatacg a                                              21

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
tcggtggtcg ccgtatcatt                                                20

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
tcgtatgccg tcttctgctt g                                              21

<210> SEQ ID NO 5
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (23)..(23)
<223> OTHER INFORMATION: n=uracil
<220> FEATURE:
<221> NAME/KEY: misc_feature
<222> LOCATION: (23)..(23)
<223> OTHER INFORMATION: n is a, c, g, or t

<400> SEQUENCE: 5
aatgatacgg cgaccaccga ganctacac                                      29

<210> SEQ ID NO 6
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (22)..(22)
<223> OTHER INFORMATION: 8-oxo-guanosine

<400> SEQUENCE: 6
caagcagaag acggcatacg agat                                           24

<210> SEQ ID NO 7
<211> LENGTH: 29
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 7
gtgtagatct cggtggtcgc cgtatcatt                                    29

<210> SEQ ID NO 8
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 8
atctcgtatg ccgtcttctg cttg                                         24
```